(12) United States Patent
Cruise et al.

(10) Patent No.: US 10,946,100 B2
(45) Date of Patent: Mar. 16, 2021

(54) POLYMERS INCLUDING ACTIVE AGENTS

(71) Applicant: MicroVention, Inc., Aliso Viejo, CA (US)

(72) Inventors: Gregory M. Cruise, Rancho Santa Margarita, CA (US); Clayton G. Harris, Aliso Viejo, CA (US); Michael J. Constant, Mission Viejo, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

(21) Appl. No.: 16/250,878

(22) Filed: Jan. 17, 2019

(65) Prior Publication Data
US 2019/0151452 A1 May 23, 2019

Related U.S. Application Data

(62) Division of application No. 14/678,514, filed on Apr. 3, 2015, now Pat. No. 10,226,533.

(60) Provisional application No. 61/986,015, filed on Apr. 29, 2014.

(51) Int. Cl.
| | | |
|---|---|---|
| A61K 47/32 | (2006.01) |
| A61K 9/70 | (2006.01) |
| A61K 31/7068 | (2006.01) |
| A61K 31/787 | (2006.01) |
| C07H 19/06 | (2006.01) |
| C07F 15/00 | (2006.01) |
| A61L 31/14 | (2006.01) |
| A61L 31/16 | (2006.01) |
| A61L 31/18 | (2006.01) |
| A61K 9/00 | (2006.01) |
| A61K 49/04 | (2006.01) |
| A61K 47/58 | (2017.01) |

(52) U.S. Cl.
CPC ............ *A61K 47/32* (2013.01); *A61K 9/0092* (2013.01); *A61K 31/7068* (2013.01); *A61K 31/787* (2013.01); *A61K 47/58* (2017.08); *A61K 49/04* (2013.01); *A61L 31/145* (2013.01); *A61L 31/148* (2013.01); *A61L 31/16* (2013.01); *A61L 31/18* (2013.01); *C07F 15/0093* (2013.01); *C07H 19/06* (2013.01); *A61L 2430/36* (2013.01)

(58) Field of Classification Search
CPC ... A61K 31/7068; A61K 31/787; A61L 31/18; A61L 49/04
See application file for complete search history.

(56) References Cited

U.S. PATENT DOCUMENTS

| | | |
|---|---|---|
| 3,709,842 A | 1/1973 | Stoy et al. |
| 3,743,686 A | 7/1973 | Koch et al. |
| 3,749,085 A | 7/1973 | Wilson et al. |
| 4,020,829 A | 5/1977 | Wilson et al. |
| 4,301,803 A | 11/1981 | Handa et al. |
| 4,304,232 A | 12/1981 | Michaels |
| 4,365,621 A | 12/1982 | Brundin |
| 4,402,319 A | 9/1983 | Handa et al. |
| 4,493,329 A | 1/1985 | Crawford et al. |
| 4,509,504 A | 4/1985 | Brundin |
| 4,529,739 A | 7/1985 | Scott et al. |
| 4,551,132 A | 11/1985 | Pasztor et al. |
| 4,663,358 A | 5/1987 | Hyon et al. |
| 4,795,741 A | 1/1989 | Leshchiner et al. |
| 4,819,637 A | 4/1989 | Dormandy, Jr. et al. |
| 4,932,419 A | 6/1990 | de Toledo |
| 4,951,677 A | 8/1990 | Crowley et al. |
| 4,994,069 A | 2/1991 | Ritchart et al. |
| 5,120,349 A | 6/1992 | Stewart et al. |
| 5,122,136 A | 6/1992 | Guglielmi et al. |
| 5,129,180 A | 7/1992 | Stewart |
| 5,133,731 A | 7/1992 | Butler et al. |
| 5,147,646 A | 9/1992 | Graham |
| 5,154,705 A | 10/1992 | Fleischhacker et al. |
| 5,163,952 A | 11/1992 | Froix |
| 5,165,421 A | 11/1992 | Fleischhacker et al. |
| 5,217,484 A | 6/1993 | Marks |
| 5,226,911 A | 7/1993 | Chee et al. |
| 5,258,042 A | 11/1993 | Mehta |
| 5,304,194 A | 4/1994 | Chee et al. |
| 5,312,415 A | 5/1994 | Palermo |
| 5,350,397 A | 9/1994 | Palermo et al. |
| 5,354,290 A | 10/1994 | Gross |
| 5,373,619 A | 12/1994 | Fleischhacker et al. |
| 5,382,259 A | 1/1995 | Phelps et al. |
| 5,382,260 A | 1/1995 | Dormandy, Jr. et al. |
| 5,443,478 A | 8/1995 | Purdy |
| 5,447,727 A | 9/1995 | Graham |
| 5,449,369 A | 9/1995 | Imran |
| 5,456,693 A | 10/1995 | Conston et al. |
| 5,469,867 A | 11/1995 | Schmitt |
| 5,476,472 A | 12/1995 | Dormandy, Jr. et al. |

(Continued)

FOREIGN PATENT DOCUMENTS

| CA | 2551373 C | 6/2014 |
|---|---|---|
| CN | 102107025 B | 5/2014 |

(Continued)

OTHER PUBLICATIONS

Ahuja et al., Platinum coil coatings to increase thrombogenicity: a preliminary study in rabbits, AJNR, 14: 794-789 (1993).

(Continued)

*Primary Examiner* — Kyle A Purdy
(74) *Attorney, Agent, or Firm* — K&L Gates LLP; Brian J. Novak; Louis C. Cullman

(57) ABSTRACT

Polymers are described herein comprising: a reaction product of a prepolymer solution including at least one macromer and at least one visualization agent; and an active agent electrostatically bound to the polymer filament or chemically bound to the at least one monomer; wherein the polymer filament does not include metallic support members.

23 Claims, 1 Drawing Sheet

(56) References Cited

U.S. PATENT DOCUMENTS

| | | |
|---|---|---|
| 5,483,022 A | 1/1996 | Mar |
| 5,508,342 A | 4/1996 | Antonucci |
| 5,522,822 A | 6/1996 | Phelps et al. |
| 5,525,334 A | 6/1996 | Ito et al. |
| 5,536,274 A | 7/1996 | Neuss |
| 5,538,512 A | 7/1996 | Zenzen |
| 5,539,071 A | 7/1996 | Staffler |
| 5,541,234 A | 7/1996 | Unger et al. |
| 5,549,624 A | 8/1996 | Mirigian |
| 5,567,435 A | 10/1996 | Hubbell et al. |
| 5,573,520 A | 11/1996 | Schwartz et al. |
| 5,573,994 A | 11/1996 | Kabra et al. |
| 5,578,074 A | 11/1996 | Mirigian |
| 5,580,568 A | 12/1996 | Greff et al. |
| 5,582,610 A | 12/1996 | Grossi et al. |
| 5,582,619 A | 12/1996 | Ken |
| 5,603,991 A | 2/1997 | Kupiecki et al. |
| 5,607,417 A | 3/1997 | Batich et al. |
| 5,609,629 A | 3/1997 | Fearnot et al. |
| 5,612,050 A | 3/1997 | Rowe et al. |
| 5,624,461 A | 4/1997 | Mariant |
| 5,624,685 A | 4/1997 | Takahashi et al. |
| 5,634,936 A | 6/1997 | Linden et al. |
| 5,645,558 A | 7/1997 | Horton |
| 5,651,979 A | 7/1997 | Ron et al. |
| 5,658,308 A | 8/1997 | Snyder |
| 5,667,767 A | 9/1997 | Greff et al. |
| 5,672,634 A | 9/1997 | Tseng et al. |
| 5,677,067 A | 10/1997 | Kojima |
| 5,678,296 A | 10/1997 | Fleischhacker et al. |
| 5,690,666 A | 11/1997 | Berenstein et al. |
| 5,690,667 A | 11/1997 | Gia |
| 5,690,671 A | 11/1997 | McGurk et al. |
| 5,695,480 A | 12/1997 | Evans et al. |
| 5,702,361 A | 12/1997 | Evans et al. |
| 5,718,711 A | 2/1998 | Berenstein et al. |
| 5,725,568 A | 3/1998 | Hastings |
| 5,749,894 A | 5/1998 | Engelson |
| 5,750,585 A | 5/1998 | Park et al. |
| 5,752,974 A | 5/1998 | Rhee et al. |
| 5,755,658 A | 5/1998 | Wallace et al. |
| 5,766,160 A | 6/1998 | Samson et al. |
| 5,766,219 A | 6/1998 | Horton |
| 5,823,198 A | 10/1998 | Jones et al. |
| 5,827,231 A | 10/1998 | Harada |
| 5,830,178 A | 11/1998 | Jones et al. |
| 5,834,118 A | 11/1998 | Rangnby |
| 5,843,743 A | 12/1998 | Hubbell et al. |
| 5,851,508 A | 12/1998 | Greff et al. |
| 5,853,418 A | 12/1998 | Ken |
| 5,853,419 A | 12/1998 | Ken et al. |
| 5,863,551 A | 1/1999 | Woerly |
| 5,883,705 A | 3/1999 | Minne et al. |
| 5,891,155 A | 4/1999 | Irie |
| 5,952,232 A | 9/1999 | Rothman |
| 5,976,162 A | 11/1999 | Doan et al. |
| 5,980,514 A | 11/1999 | Kupiecki et al. |
| 6,004,338 A | 12/1999 | Ken et al. |
| 6,004,573 A | 12/1999 | Rathi et al. |
| 6,013,084 A | 1/2000 | Ken et al. |
| 6,015,424 A | 1/2000 | Rosenbluth et al. |
| 6,017,977 A | 1/2000 | Evans et al. |
| 6,051,607 A | 4/2000 | Greff |
| 6,063,100 A | 5/2000 | Diaz et al. |
| 6,066,149 A | 5/2000 | Samson et al. |
| 6,093,199 A | 7/2000 | Brown et al. |
| 6,096,034 A | 8/2000 | Kupiecki et al. |
| 6,103,865 A | 8/2000 | Bae et al. |
| 6,136,015 A | 10/2000 | Kurz et al. |
| 6,146,373 A | 11/2000 | Cragg et al. |
| 6,159,165 A | 12/2000 | Ferrera et al. |
| 6,168,570 B1 | 1/2001 | Ferrera |
| 6,171,326 B1 | 1/2001 | Ferrera et al. |
| 6,179,857 B1 | 1/2001 | Diaz et al. |
| 6,187,024 B1 | 2/2001 | Boock et al. |
| 6,193,728 B1 | 2/2001 | Ken et al. |
| 6,201,065 B1 | 3/2001 | Pathak et al. |
| 6,224,893 B1 | 5/2001 | Langer |
| 6,231,590 B1 | 5/2001 | Slaikeu et al. |
| 6,238,403 B1 | 5/2001 | Greene, Jr. et al. |
| 6,245,090 B1 | 6/2001 | Gilson et al. |
| 6,270,748 B1 | 8/2001 | Annan et al. |
| 6,280,457 B1 | 8/2001 | Wallace et al. |
| 6,281,263 B1 | 8/2001 | Evans et al. |
| 6,287,318 B1 | 9/2001 | Villar et al. |
| 6,299,604 B1 | 10/2001 | Ragheb et al. |
| 6,299,619 B1 | 10/2001 | Greene, Jr. et al. |
| 6,299,627 B1 | 10/2001 | Eder et al. |
| 6,303,100 B1 | 10/2001 | Ricci et al. |
| 6,312,421 B1 | 11/2001 | Boock |
| 6,333,020 B1 | 12/2001 | Wallace et al. |
| 6,335,384 B1 | 1/2002 | Evans et al. |
| 6,342,202 B1 | 1/2002 | Evans et al. |
| 6,342,541 B1 | 1/2002 | Lombradi |
| 6,375,880 B1 | 4/2002 | Cooper |
| 6,399,886 B1 | 6/2002 | Avellanet |
| 6,423,085 B1 | 7/2002 | Murayama et al. |
| 6,425,893 B1 | 7/2002 | Guglielmi et al. |
| 6,454,738 B1 | 9/2002 | Tran et al. |
| 6,503,244 B2 | 1/2003 | Hayman |
| 6,511,468 B1 | 1/2003 | Cragg et al. |
| 6,511,472 B1 | 1/2003 | Hayman et al. |
| 6,531,111 B1 | 3/2003 | Whalen et al. |
| 6,537,569 B2 | 3/2003 | Cruise et al. |
| 6,558,367 B1 | 5/2003 | Cragg et al. |
| 6,565,551 B1 | 5/2003 | Jones et al. |
| 6,569,190 B2 | 5/2003 | Whalen et al. |
| 6,599,448 B1 | 7/2003 | Ehrhard, Jr. et al. |
| 6,602,261 B2 | 8/2003 | Greene, Jr. et al. |
| 6,605,294 B2 | 8/2003 | Sawhney |
| 6,623,450 B1 | 9/2003 | Dutta |
| 6,634,361 B1 | 10/2003 | Nikolchev et al. |
| 6,645,167 B1 | 11/2003 | Whalen et al. |
| 6,684,884 B2 | 2/2004 | Nikolchev et al. |
| 6,699,222 B1 | 3/2004 | Jones et al. |
| 6,723,108 B1 | 4/2004 | Jones et al. |
| 6,756,031 B2 | 6/2004 | Evans et al. |
| 6,759,028 B2 | 7/2004 | Wallace et al. |
| 6,849,081 B2 | 2/2005 | Sepetka et al. |
| 6,860,893 B2 | 3/2005 | Wallace et al. |
| 6,878,384 B2 | 4/2005 | Cruise et al. |
| 6,887,974 B2 | 5/2005 | Pathak et al. |
| 6,962,689 B2 | 11/2005 | Whalen et al. |
| 6,964,657 B2 | 11/2005 | Cragg et al. |
| 7,018,365 B2 | 3/2006 | Strauss et al. |
| 7,033,374 B2 | 4/2006 | Schaefer et al. |
| 7,066,904 B2 | 6/2006 | Rosenthal et al. |
| 7,070,607 B2 | 7/2006 | Murayama et al. |
| 7,083,643 B2 | 8/2006 | Whalen et al. |
| 7,138,106 B2 | 11/2006 | Evans et al. |
| 7,374,568 B2 | 5/2008 | Whalen et al. |
| 7,422,569 B2 | 9/2008 | Wilson et al. |
| 7,459,142 B2 | 12/2008 | Greff |
| 7,476,648 B1 | 1/2009 | Tabata et al. |
| 7,507,229 B2 | 3/2009 | Hewitt et al. |
| 7,507,394 B2 | 3/2009 | Whalen et al. |
| 7,625,580 B1 | 12/2009 | Langer |
| 7,815,835 B2 | 10/2010 | Stampfl |
| 7,976,527 B2 | 7/2011 | Cragg et al. |
| 7,988,992 B2 | 8/2011 | Omidian et al. |
| 8,066,667 B2 | 11/2011 | Hayman et al. |
| 8,183,229 B2 | 5/2012 | Hahn |
| 8,235,941 B2 | 8/2012 | Hayman et al. |
| 8,377,091 B2 | 2/2013 | Cruise et al. |
| 8,454,649 B2 | 6/2013 | Cragg et al. |
| 8,486,046 B2 | 7/2013 | Hayman et al. |
| 9,011,884 B2 | 4/2015 | Constant et al. |
| 2001/0023325 A1 | 9/2001 | Ferrera |
| 2002/0026234 A1 | 2/2002 | Li et al. |
| 2002/0042378 A1 | 4/2002 | Reich et al. |
| 2002/0169473 A1 | 11/2002 | Sepetka et al. |
| 2002/0176880 A1 | 11/2002 | Cruise et al. |
| 2003/0021762 A1 | 1/2003 | Luthra et al. |
| 2003/0036582 A1 | 2/2003 | Yamakawa |

(56) References Cited

U.S. PATENT DOCUMENTS

| | | |
|---|---|---|
| 2003/0077272 A1 | 4/2003 | Pathak et al. |
| 2003/0078339 A1 | 4/2003 | Kiser et al. |
| 2003/0086874 A1 | 5/2003 | Whalen, II et al. |
| 2003/0100942 A1 | 5/2003 | Ken et al. |
| 2003/0134032 A1 | 7/2003 | Chaouk |
| 2003/0162863 A1 | 8/2003 | Satoh |
| 2003/0203991 A1 | 10/2003 | Schottman et al. |
| 2003/0211083 A1 | 11/2003 | Vogel et al. |
| 2003/0220245 A1 | 11/2003 | Hubbell et al. |
| 2003/0232198 A1 | 12/2003 | Lamberti et al. |
| 2003/0232895 A1 | 12/2003 | Omidian et al. |
| 2004/0006534 A1 | 1/2004 | Schaefer et al. |
| 2004/0024098 A1 | 2/2004 | Mather et al. |
| 2004/0059370 A1 | 3/2004 | Greene et al. |
| 2004/0091543 A1 | 5/2004 | Bell et al. |
| 2004/0097267 A1 | 5/2004 | Vallittu |
| 2004/0098028 A1 | 5/2004 | Martinez |
| 2004/0115164 A1 | 6/2004 | Pierce et al. |
| 2004/0158282 A1 | 8/2004 | Jones et al. |
| 2004/0209998 A1 | 10/2004 | De Vries |
| 2004/0242713 A1 | 12/2004 | Ghidoni |
| 2004/0247867 A1 | 12/2004 | Chaouk et al. |
| 2005/0003010 A1 | 1/2005 | Cohen et al. |
| 2005/0008610 A1 | 1/2005 | Schwarz et al. |
| 2005/0095428 A1 | 5/2005 | DiCarlo et al. |
| 2005/0106119 A1 | 5/2005 | Brandom et al. |
| 2005/0119687 A1 | 6/2005 | Dacey et al. |
| 2005/0124721 A1 | 6/2005 | Arthur et al. |
| 2005/0143484 A1 | 6/2005 | Fang et al. |
| 2005/0171572 A1 | 8/2005 | Martinez et al. |
| 2005/0175709 A1 | 8/2005 | Baty et al. |
| 2005/0196426 A1 | 9/2005 | Cruise et al. |
| 2005/0196449 A1 | 9/2005 | DiCarlo et al. |
| 2005/0226935 A1 | 10/2005 | Kamath et al. |
| 2005/0281883 A1 | 12/2005 | Daniloff et al. |
| 2006/0052815 A1 | 3/2006 | Fitz et al. |
| 2006/0067883 A1 | 3/2006 | Krom et al. |
| 2006/0074370 A1 | 4/2006 | Zhou |
| 2006/0233854 A1 | 10/2006 | Seliktar et al. |
| 2006/0270750 A1 | 11/2006 | Almen et al. |
| 2007/0026039 A1 | 2/2007 | Drumheller et al. |
| 2007/0097627 A1 | 5/2007 | Taylor |
| 2007/0196454 A1 | 8/2007 | Stockman et al. |
| 2007/0202046 A1 | 8/2007 | Dave |
| 2007/0208141 A1 | 9/2007 | Shull et al. |
| 2007/0224234 A1 | 9/2007 | Steckel et al. |
| 2007/0231366 A1 | 10/2007 | Sawhney et al. |
| 2007/0237720 A1 | 10/2007 | Padilla et al. |
| 2007/0237741 A1 | 10/2007 | Figuly et al. |
| 2007/0248567 A1 | 10/2007 | Pathak et al. |
| 2007/0254005 A1 | 11/2007 | Pathak et al. |
| 2007/0288084 A1 | 12/2007 | Lee et al. |
| 2008/0019921 A1 | 1/2008 | Zhang |
| 2008/0038354 A1 | 2/2008 | Slager et al. |
| 2008/0039890 A1 | 2/2008 | Matson et al. |
| 2008/0114277 A1 | 5/2008 | Ambrosio et al. |
| 2008/0208167 A1 | 8/2008 | Stankus |
| 2008/0226741 A1 | 9/2008 | Richard |
| 2008/0268250 A1 | 10/2008 | Hawkett |
| 2008/0281352 A1 | 11/2008 | Ingenito et al. |
| 2009/0041850 A1 | 2/2009 | Figuly |
| 2009/0048659 A1 | 2/2009 | Weber et al. |
| 2009/0054535 A1 | 2/2009 | Figuly et al. |
| 2009/0081275 A1 | 3/2009 | Rolfes et al. |
| 2009/0093550 A1 | 4/2009 | Rolfes et al. |
| 2009/0098510 A1 | 4/2009 | Zhang |
| 2009/0117033 A1 | 5/2009 | O'Gara |
| 2009/0164013 A1 | 6/2009 | Cruise et al. |
| 2009/0181068 A1 | 7/2009 | Dunn |
| 2009/0221731 A1 | 9/2009 | Vetrecin et al. |
| 2009/0224438 A1 | 9/2009 | Stampfl |
| 2009/0232869 A1 | 9/2009 | Greene |
| 2009/0239962 A1 | 9/2009 | Dobashi |
| 2009/0258979 A1 | 10/2009 | Hawkett |
| 2009/0259302 A1 | 10/2009 | Trollsas et al. |
| 2010/0010159 A1 | 1/2010 | Belcheva |
| 2010/0023112 A1 | 1/2010 | Borck et al. |
| 2010/0036491 A1 | 2/2010 | He et al. |
| 2010/0042067 A1 | 2/2010 | Koehler |
| 2010/0048750 A1 | 2/2010 | Blom |
| 2010/0086678 A1 | 4/2010 | Arthur et al. |
| 2010/0092533 A1 | 4/2010 | Stopek et al. |
| 2010/0241160 A1 | 9/2010 | Murphy |
| 2010/0247663 A1 | 9/2010 | Day et al. |
| 2010/0249913 A1 | 9/2010 | Dattaa et al. |
| 2010/0256777 A1 | 10/2010 | Dattta et al. |
| 2010/0303804 A1 | 12/2010 | Liska et al. |
| 2011/0008406 A1 | 1/2011 | Altman et al. |
| 2011/0008442 A1 | 1/2011 | Zawko et al. |
| 2011/0020236 A1 | 1/2011 | Bohmer et al. |
| 2011/0027172 A1 | 2/2011 | Wang et al. |
| 2011/0091549 A1 | 4/2011 | Blaskovich et al. |
| 2011/0182998 A1 | 7/2011 | Reb et al. |
| 2011/0184455 A1 | 7/2011 | Keeley |
| 2011/0190813 A1 | 8/2011 | Brownlee et al. |
| 2011/0202016 A1 | 8/2011 | Zugates et al. |
| 2011/0212178 A1 | 9/2011 | Constant et al. |
| 2012/0029101 A1 | 2/2012 | Senda |
| 2012/0041481 A1 | 2/2012 | Daniloff et al. |
| 2012/0083523 A1 | 4/2012 | Richard et al. |
| 2012/0114589 A1 | 5/2012 | Rolfes-Meyering et al. |
| 2012/0156164 A1 | 6/2012 | Park et al. |
| 2012/0164100 A1 | 6/2012 | Li et al. |
| 2012/0184642 A1 | 7/2012 | Bartling et al. |
| 2012/0238644 A1 | 9/2012 | Gong et al. |
| 2012/0244198 A1 | 9/2012 | Malmsjo et al. |
| 2012/0283769 A1 | 11/2012 | Cruise et al. |
| 2012/0289995 A1 | 11/2012 | Constant et al. |
| 2013/0039848 A1 | 2/2013 | Bradbury et al. |
| 2013/0045182 A1 | 2/2013 | Gong et al. |
| 2013/0060230 A1 | 3/2013 | Capistron |
| 2013/0079421 A1 | 3/2013 | Aviv et al. |
| 2013/0087736 A1 | 4/2013 | Baker |
| 2013/0108574 A1 | 5/2013 | Chevalier et al. |
| 2013/0131716 A1 | 5/2013 | Cruise et al. |
| 2013/0253087 A1 | 9/2013 | Cruise et al. |
| 2014/0056806 A1 | 2/2014 | Vemengo et al. |
| 2014/0274945 A1 | 9/2014 | Blaskovich et al. |
| 2014/0277057 A1 | 9/2014 | Ortega et al. |
| 2014/0329932 A1 | 11/2014 | Baker |
| 2015/0190553 A1 | 7/2015 | Constant et al. |
| 2015/0283306 A1 | 10/2015 | Constant et al. |
| 2015/0306227 A1 | 10/2015 | Cruise et al. |
| 2015/0306255 A1 | 10/2015 | Constant et al. |
| 2016/0166258 A1 | 6/2016 | Cruise et al. |
| 2016/0345978 A1 | 12/2016 | Cruise et al. |
| 2016/0361459 A1 | 12/2016 | Baldwin |
| 2016/0367730 A1 | 12/2016 | Constant et al. |
| 2017/0007264 A1 | 1/2017 | Cruise et al. |
| 2017/0290593 A1 | 10/2017 | Cruise et al. |
| 2018/0110527 A1 | 4/2018 | Cruise et al. |
| 2019/0150932 A1 | 5/2019 | Cruise et al. |

FOREIGN PATENT DOCUMENTS

| | | |
|---|---|---|
| EP | 809519 B1 | 12/1997 |
| EP | 1599258 B1 | 8/2008 |
| EP | 1601392 B1 | 4/2009 |
| WO | 1991/004732 A1 | 9/1990 |
| WO | 1991/016057 A | 10/1991 |
| WO | 1994/003155 A1 | 2/1994 |
| WO | 1997/022365 A1 | 6/1997 |
| WO | 1997/026939 A1 | 7/1997 |
| WO | 1997/027888 A1 | 8/1997 |
| WO | 1998/001421 A1 | 1/1998 |
| WO | 1998/043615 A1 | 10/1998 |
| WO | 1998/055103 A1 | 12/1998 |
| WO | 1999/023954 A1 | 5/1999 |
| WO | 1999/044538 A1 | 9/1999 |
| WO | 1999/056783 A1 | 11/1999 |
| WO | 1999/065401 A1 | 12/1999 |
| WO | 2000/027445 A1 | 5/2000 |
| WO | 2000/038651 A1 | 7/2000 |
| WO | 2000/074577 A1 | 12/2000 |

(56) References Cited

FOREIGN PATENT DOCUMENTS

| WO | 2001/068720 A1 | 9/2001 |
| WO | 2002/005731 A1 | 1/2002 |
| WO | 2002/096302 A1 | 12/2002 |
| WO | 2003/043552 A1 | 5/2003 |
| WO | 2005/032337 A2 | 4/2005 |
| WO | 2007/016371 A2 | 2/2007 |
| WO | 2007/147145 A2 | 12/2007 |
| WO | 2000/078846 A1 | 12/2008 |
| WO | 2009/086208 A2 | 7/2009 |
| WO | 2011/038291 A1 | 3/2011 |
| WO | 2011/053555 A1 | 5/2011 |
| WO | 2012/039602 A1 | 3/2012 |
| WO | 2012/101455 A1 | 8/2012 |
| WO | 2012/120138 A1 | 9/2012 |
| WO | 2012/145431 A3 | 10/2012 |
| WO | 2012/171478 A1 | 12/2012 |
| WO | 2013/158781 | 10/2013 |
| WO | 2015/153996 A1 | 10/2015 |
| WO | 2015/167751 A1 | 11/2015 |
| WO | 2015/167752 A1 | 11/2015 |
| WO | 2016/201250 A1 | 12/2016 |

OTHER PUBLICATIONS

Almany, Biomaterials, 26, 2005, 2467-2477, Biosynthetic hydrogel scaffolds made from fibrinogen and polyethylene glycol for 3D cell cultures.

Carelli V. et al., "Silicone microspheres for pH-controlled gastrointestinal drug delivery," 1999, International Journal of Pharmaceutics, V179, p. 73-83.

Chirila et al., Poly(2-hydroxyethyl metharcrylate) sponges ans implant materials: in vivo and in vitro evaluation of cellular invasion. Biomaterials, 14(1):26-38 (1993).

Constant et al., Preparation, Characterization, and Evaluation of Radiopaque Hydrogel Filaments for Endovascular Embolization. Journal of Biomedical Materials Research Part B: Applied Biomaterials, vol. 89B, No. 2, pp. 306-313 (2008).

Edleman et al., Controlled and modulated release of basic fibroblast growth factor. Biomaterials, vol. 12, pp. 619-626 (1991).

Elbert et al., Conjugate addition reactions combined with free-radical cross-linking for the design of materials for tissue engineering. Biomacromolecules, (2): 430-441 (2001).

European Search Opinion for EP Application No. 10819570 dated Mar. 31, 2014.

European Search Opinion for EP Application No. 10827370 dated Apr. 1, 2014.

Graves et al., Endovascular occlusion of the carotid or vertebral artery with temporary proximal flow arrest and mircocoils: clinical results. AJNR Am. J. Neuroradiol, vol. 18, pp. 1201-1206 (1997).

Hoekstra, D., Hyaluronan-modified surfaces for medical devices. Medical Device & Diagnostic Industry, pp. 48-56 (1999).

Hogg et al., Interaction of platelet-derived growth factor with thrombospondin 1. Biochem. J. 326, pp. 709-716 (1997).

Horak et al., Hydrogels in endovascular embolization. II. Clinical use of spherical particles. Biomaterials, 7(6): 467-470 (1986).

Horak et al., New radiopaque polyHEMA-based hydrogel particles. J. Biomed. Matter Res., 34(2): 183-188 (1997).

Huang, et al., "Synthesis and Characterization of Self-Assembling Block Copolymers Containing Adhesive Molecules," Polymer Preprints, vol. 42, No. 2, 2001, pp. 147-148.

International Search Report dated Dec. 17, 2010 for International Patent Application No. PCT/US2010/053972.

International Search Report dated Feb. 5, 2009 for International Patent Application No. PCT/US2007/071395.

International Search Report dated Aug. 14, 2013 for International PCT Application No. PCT/US2013/037007 filed on Apr. 17, 2013.

International Search Report and Written Opinion dated Jun. 29, 2015 for International Application No. PCT/US2015/024289 filed on Apr. 3, 2015.

International Search Report and Written Opinion dated Jun. 29, 2015 for International Application No. PCT/US2015/024290 filed on Apr. 3, 2015.

International Search Report and Written Opinion dated Jul. 14, 2015 for International Application No. PCT/US2015/024284 filed on Apr. 3, 2015.

Kim, Drug release from pH-sensitive interpenetrating polymer networks hydrogel based on poly (ethylene glycol) Macromer and Poly (acrylic acid) prepared by UV Cured Method, ArchPharmRes, vol. 19(1), 1996, p. 18-22.

Klier, Self Associating Networks of Poly(methacrylic acid g-ethylene glycol) Marcomolecules 1990, vol. 23, 1990, p. 1944-4949.

Larsen et al., Hylan gel composition for percutaneous embolization. Journal of Biomedical Materials Research, vol. 25, Issue 6, pp. 699-710 (1991).

Latchaw et al., Polyvinyl foam embolization of vascular and neoplastic lesions of the head, neck, and spine. Radiology, 131: 669-679 (1979).

Li, Jian et al., Preparation of PEG/Aac copolymerric hydrogel and study of pH-sensitivity. Chemistry World, Issue 1, pp. 20-23 (2005).

Mellott, Michael B. et al., Release of protein from highly cross-linked hydrogels of poly(ethylene glycol) diacrylate fabricated by UV polymerization. Biomaterials, 22(2001) 929-941.

Murayama et al., Cellular responses of bioabsorbable polymeric material and guglielmi detachable coil in experimental aneurysms. Stroke, pp. 1120-1128 (2002).

Persidis, A., Tissue engineering. Nature Biotechnology, 17, pp. 508-510 (1999).

Schmutz et al., Embolization of cerebral arteriovenous malformations with silk: histopathologic changes and hemorrhagic complications. AJNR Am. J. Neuroradiol., vol. 18, pp. 1233-1237 (1997).

Schoenmakers, The effect of the linker on the hydrolysis rate of drug-linked ester bonds, J. Cont. Rel., 95, 2004, pp. 291-300.

Supplementary European Search Report for EP Application No. 10819570 dated Mar. 31, 2014.

Supplementary European Search Report for EP Application No. 10827370 dated Apr. 1, 2014.

Vinuela et al., Guglielmi detachable coil embolization of acute intracranial aneurysm: perioperative anatomical and clinical outcome in 403 patients. J. Neurosurg., vol. 86, pp. 475-482 (1997).

Woerly et al., Intracerebral implantation of hydrogel-coupled adhesion peptides: tissue reaction. Journal of Neural Transplantation & Plasticity, vol. 5, No. 4, pp. 245-255 (1995).

Written Opinion dated Aug. 14, 2013 for International PCT Application No. PCT/US2013/037007 filed on Apr. 17, 2013.

Zollikofer et al., A combination of stainless steel coil and compressed ivalon: a new technique for embolization of larger arteries and arteriovenous fistulas. Radiology, 138: 229-231 (1981).

Zollikofer et al., Therapeutic blockade of arteries using compressed invalon. Radiology, 136: 635-640 (1980).

Son et al., Preparation of properties of PEG-modified PHEMA hydrogel and the morphological effect. Macromolecular Research, vol. 14, No. 3, pp. 394-399 (2006).

International Search Report and Written Opinion dated Sep. 23, 2016 for International Application No. PCT/US2016/036924 filed on Jun. 10, 2016.

Supplementary European Search Report for EP Application No. 15785350 dated Nov. 13, 2017.

"Wavy line", Illustrated Glossary of Organic Chemistry, accessed at http://www.chem.ucla.edu/~harding/IGOC/W/wavy_line.html on Jul. 21, 2016.

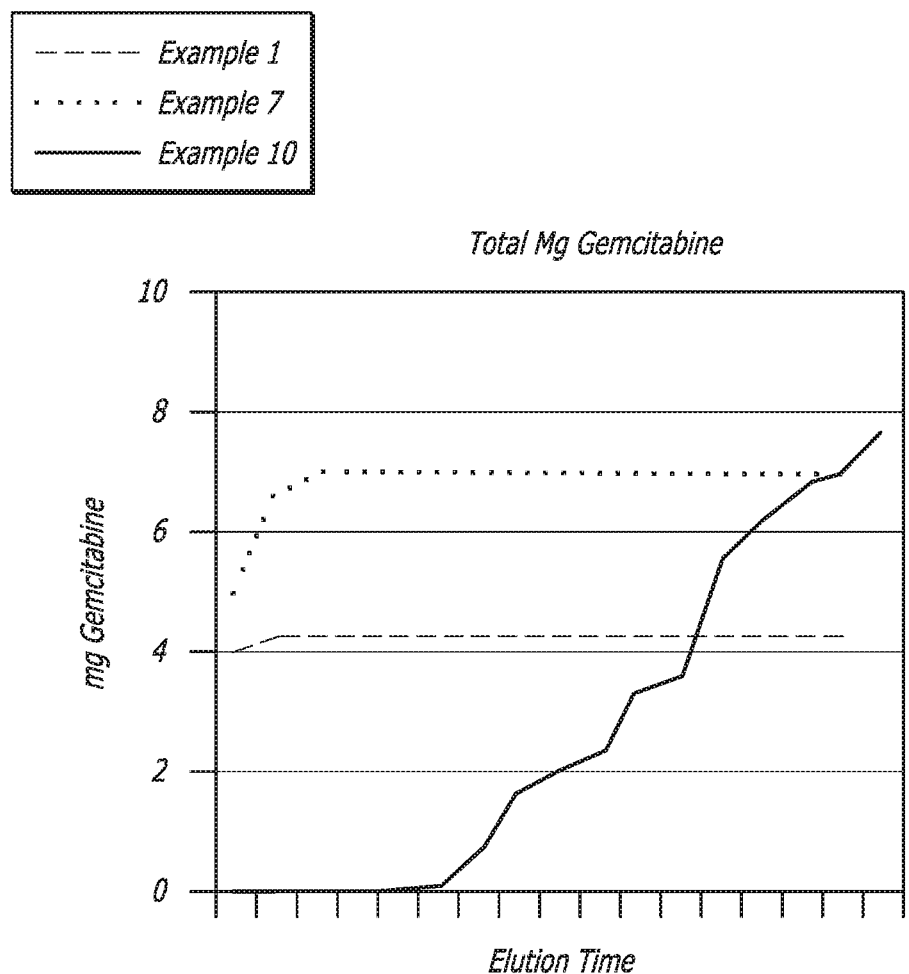

POLYMERS INCLUDING ACTIVE AGENTS

CROSS REFERENCE TO RELATED APPLICATIONS

This application is a divisional of U.S. patent application Ser. No. 14/678,514, filed Apr. 3, 2015, which claims the benefit of U.S. provisional patent application No. 61/986,015, filed Apr. 29, 2014, the entire disclosures each of which is incorporated herein by reference.

FIELD

The present description provides polymers and polymer filaments for the occlusion of vascular sites and cavities within the body, such as the embolization of vascularized tumors or arteriovenous malformations including active pharmaceutical agents that can be released in situ.

SUMMARY

Described herein generally are polymer and/or hydrogel filaments configured to deliver pharmaceutical agents in situ. These polymers and/or hydrogels can also be optionally configured for embolization. In other embodiments, the polymers and/or hydrogels can be delivered in such a manner not to substantially occlude flow through a vessel or other lumen.

The polymer filaments can include one or more monomers and/or macromers and a pharmaceutical agent(s) or other active agent(s). The polymer can optionally include a visualization agent. The pharmaceutical agent can be entrapped inside the polymers, loaded into the polymers after polymerization, or the pharmaceutical agent can be modified to permit polymerization into the polymers and released over time.

To entrap the pharmaceutical agent in a polymer, the pharmaceutical agent can be dissolved into a pre-polymerization solution. As the polymerization of the polymer occurs, the pharmaceutical agent is entrapped by the polymer network. Then, once the polymer filament is delivered, the pharmaceutical agent can diffuse from the filament.

In another embodiment, when the pharmaceutical agent is loaded into the polymer after polymerization, a monomer that is capable of binding to the desired pharmaceutical agent is incorporated into the polymer and formed into a filament. Once the loaded filament is delivered, the pharmaceutical agent can diffuse from the filament.

The pharmaceutical agent itself can also be modified to permit polymerization into the polymer and release over time from the filament. For example, a polymerizable group with a degradable linkage can be attached to the pharmaceutical agent thereby permitting both polymerization into the polymer and subsequent release from the filament.

In one embodiment, a polymerizable pharmaceutical agent can have a structure

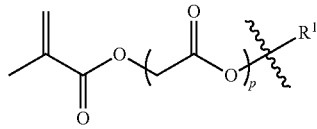

wherein $R^1$ is a pharmaceutical agent; and
p is 0, 1, 2, 3 or 4.

In some embodiments, $R^1$ is

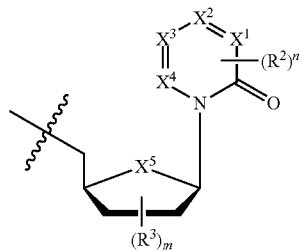

wherein each $R^2$ and $R^3$ can independently be H, $OH_3$, $C_2$-$C_6$ alkyl, $C_2$-$C_6$ substituted with a halogen or other $C_1$-$C_6$ alkyl, $NH_2$, $CO_2$, ON, $CF_3$, F, Cl, Br, I, $CCl_3$, OH, or $CH_2OH$;

n is 1, 2, 3, or 4;

m is 1, 2, 3, or 4;

$X^1$, $X^2$, $X^3$, and $X^4$ are each N or OH; and $X^5$ is O, $CH_2$, or NH.

In other embodiments, $R^1$ is

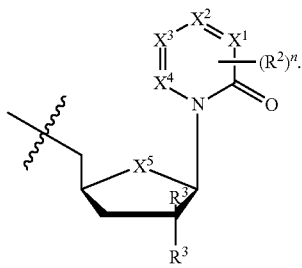

In still other embodiments, $R^1$ is

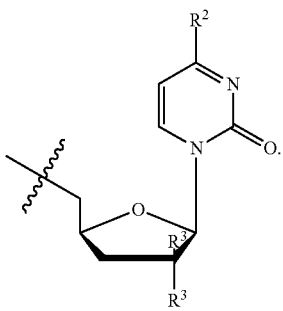

Further still, $R^1$ can be

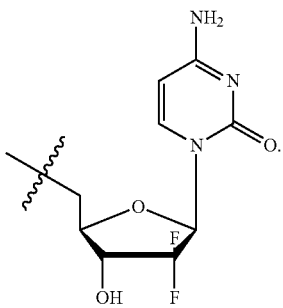

Further still, $R^1$ can be

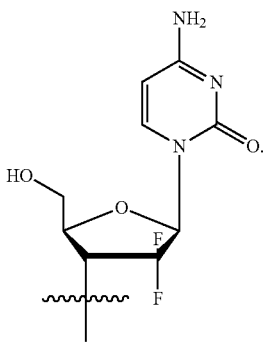

In one embodiment, a polymerizable pharmaceutical agent can have a structure

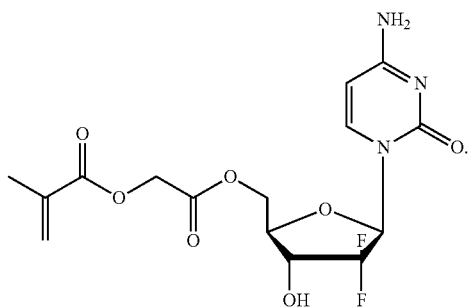

In another embodiment, a polymerizable pharmaceutical agent can have a structure

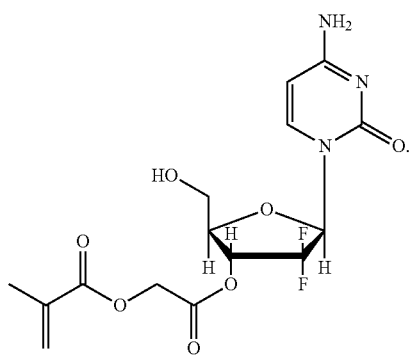

In still another embodiment, a polymerizable pharmaceutical agent can have a structure

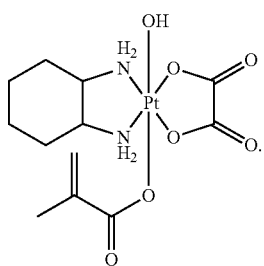

BRIEF DESCRIPTION OF THE DRAWINGS

FIG. 1 illustrates a graph of gemcitabine eluted over time.

DETAILED DESCRIPTION

Described herein are polymers such as hydrogels formed as filaments or other elongated structures that can contain one or more active agents, pharmaceutical agents, drugs and the like. Herein, active agent, pharmaceutical agent, and drug can be used interchangeably. These polymer filaments can provide controlled release of the pharmaceutical agent(s) in situ.

In one embodiment, the polymers can include (i) one or more macromers and (ii) one or more pharmaceutical agents. In another embodiment, the polymers can include (i) one or more monomers, one or more macromers, and/or one or more crosslinkers, and (ii) one or more pharmaceutical agents. In still another embodiment, the polymers can include (i) one or more crosslinkers and (ii) one or more pharmaceutical agents.

The polymers can optionally include (iii) one or more visualization agents. The polymers described can be formed from a prepolymer solution. A particular combination of monomers/macromers/crosslinkers can provide differing polymeric physical properties. Different polymeric physical properties can include, but are not limited to tensile strength, elasticity, and/or delivery through a microcatheter or catheter.

The polymers described herein can be provided as filaments or other elongated structures with round, square, rectangular, triangular, pentagonal, hexagonal, heptagonal, octagonal, ellipsoidal, rhomboidal, torx, or star-shaped cross-sectional shapes. A filament can be described as having a three dimensional shape such as, but not limited to a thread, string, hair, cylinder, fiber, or the like. The filament can be elongated meaning that its length exceeds its width or diameter by at least 5, 10, 15, 20, 50, 100, 500, 1,000, 10,000, 100,000, 1,000,000, 10,000,000, 100,000,000, or more times.

Monomers used to form the herein described polymers can have low molecular weights and/or can contain a single polymerizable group. If present, the monomer(s) can aid in polymerization and impart specific mechanical properties to the resulting polymer filament. The monomers can be any molecule with a single functionality and conducive to a desired mechanical property.

Specific monomers can include, but are not limited to, t-butyl acrylamide, 2-hydroxyethyl methacrylate, hydroxypropyl acrylate, hydroxyl butylacrylate, and derivatives thereof. The hydrophobicity and bulky structure of these specific monomers can impart column strength to the resulting polymer filament.

In some embodiments, a visualization agent can be a monomer and incorporated into the polymeric structure.

Monomers incorporating visualization characteristics can include one or more halogen atoms. For example, monomers can include 1, 2, 3, 4, 5, 6, 7 or more halogen atoms. In some embodiments, the halogen atoms can be Br or I. In one embodiment, the halogen atoms are I.

In one embodiment, a monomer including a visualization agent or the characteristics of a visualization agent can have a structure:

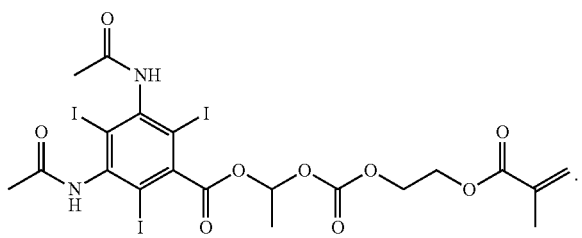 [SMILES: C=C(C)C(=O)OCCOC(=O)OC(C)OC(=O)c1c(I)c(NC(C)=O)c(I)c(NC(C)=O)c1I]

In the above structure, one or more iodine atoms can be replaced by bromine.

In another embodiment, a monomer including a visualization agent or the characteristics of a visualization agent can have a structure:

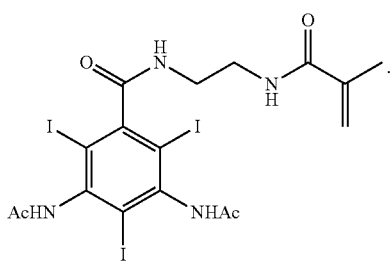 [SMILES: C=C(C)C(=O)NCCNC(=O)c1c(I)c(NC(C)=O)c(I)c(NC(C)=O)c1I]

Again, in the above structure, one or more iodine atoms can be replaced by bromine.

In another embodiment, a monomer including a visualization agent or the characteristics of a visualization agent can have a structure:

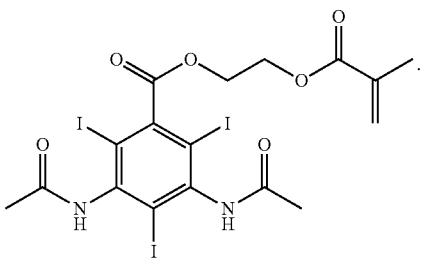 [SMILES: C=C(C)C(=O)OCCOC(=O)c1c(I)c(NC(C)=O)c(I)c(NC(C)=O)c1I]

Again, in the above structure, one or more iodine atoms can be replaced by bromine.

Monomers, if present, can be present at a concentration of about 5% w/w, about 10% w/w, about 15% w/w, about 20% w/w, about 25% w/w, about 30% w/w, about 35% w/w, about 40% w/w, about 45% w/w, about 50% w/w, at least about 5% w/w, between about 5% w/w and about 40% w/w, between about 10% w/w and about 50% w/w, between about 5% w/w and about 30% w/w, or between about 5% w/w and about 20% w/w, of the prepolymer solution.

Macromers described herein can include large molecular weight compounds such as polymers having one or more reactive groups. In some embodiments, macromers with solubility in solvents and functional groups amenable to modifications may be preferred. Polyethers, due to their solubility in a variety of solvents, their availability in a variety of forms, and their available hydroxyl groups, may be preferred macromers. Other macromers can include, but are not limited to, poly(ethylene glycol), poly(propylene glycol), and poly(tetramethylene oxide).

In other embodiments, a low molecular weight, branched macromer may be used. Such a low molecular weight, branched macromer can include at least three reactive moieties per molecule so that a high crosslink density of the finalized polymer can be achieved. Example low molecular weight, branched macromers can include ethoxylated pentaerythritol having four end groups per molecule, and ethoxylated trimethylolpropane having three end groups per molecule.

In still other embodiments, non-polyether polymers with functional groups available for modification, such as poly(vinyl alcohol), can also be used as macromers.

Macromers can be present at a concentration of about 10% w/w, about 15% w/w, about 20% w/w, about 25% w/w, about 30% w/w, about 35% w/w, about 40% w/w, about 45% w/w, about 50% w/w, at least about 10% w/w, between about 10% w/w and about 40% w/w, between about 15% w/w and about 25% w/w, between about 15% w/w and about 50% w/w, or between about 15% w/w and about 30% w/w, of the prepolymer solution. In one embodiment, the macromer concentration is about 15% w/w of the prepolymer solution.

The molecular weight of the macromer can alter the mechanical properties of the resulting polymer or hydrogel filament. In some embodiments, the alteration of the mechanical properties can be substantial. Smaller molecular weights result in polymers with sufficient column strength to be pushed through microcatheters and catheters when formed as a filament or other elongated structures. Larger molecular weights can result in polymer filaments that can be pushed through microcatheters and catheters with more difficulty. As such, the macromers described herein can have a molecular weight of about 50 g/mole, about 100 g/mole, about 200 g/mole, about 300 g/mole, about 400 g/mole, about 500 g/mole, about 1,000 g/mole, about 1,500 g/mole, about 2,000 g/mole, about 2,500 g/mole, about 3,000 g/mole, about 3,500 g/mole, about 4,000 g/mole, about 4,500 g/mole, about 5,000 g/mole, at least about 50 g/mole, at least about 100 g/mole, between about 50 g/mole and about 5,000 g/mole, between about 100 g/mole and about 5,000 g/mole, between about 1,000 g/mole and about 5,000 g/mole, between about 100 g/mole and about 1,000 g/mole, or between about 500 g/mole and about 1,000 g/mole. In one embodiment, the molecular weight is between about 500 g/mole to about 1,500 g/mole.

Crosslinkers can also be optionally utilized to impart further cross-linking of the resulting polymer. The crosslinker can be any molecule with at least two functionalities to incorporate into the resulting polymer filament. The crosslinker can also be a structure conducive to the desired mechanical property imparted on the finalized polymer filament.

Crosslinkers can also be optionally utilized to impart further cross-linking of the resulting polymer. The crosslinker can be any molecule with at least two functionalities to incorporate into the resulting polymer filament. The crosslinker can also be a structure conducive to the desired mechanical property imparted on the finalized polymer filament.

Crosslinkers can include an ester, a carbonate, a thioester, or a combination thereof. In other embodiments, multiple of each of an ester, a carbonate, a carbamate, an oxalate, and/or a thioester can be included.

Other crosslinkers can include N,N-methylenebisacrylamide and ethylene glycol dimethacrylate.

In some embodiments, biodegradable crosslinkers can be used to allow for the filament to dissolve or otherwise breakdown when placed in vivo or in another appropriate in situ condition.

In one embodiment, a biodegradable crosslinker can have a structure:

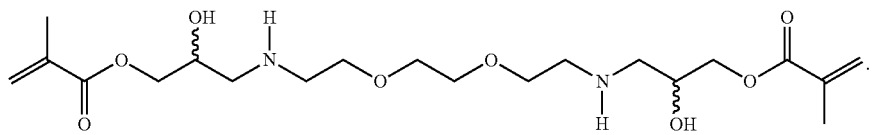 [SMILES: C=C(C)C(=O)OCC(O)CNCCOCCOCCNCC(O)COC(=O)C(=C)C]

In another embodiment, a biodegradable crosslinker can have a structure:

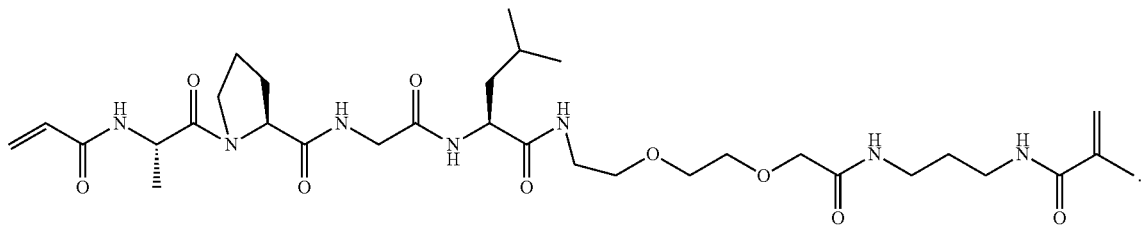

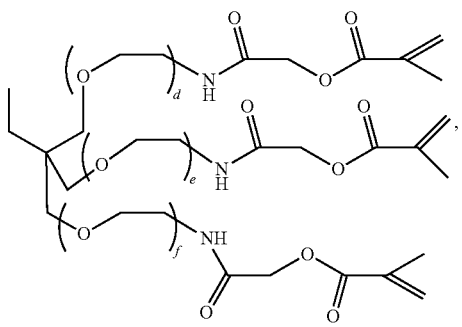

wherein d, e, f, and g are each independently 1-20.

In another embodiment, a biodegradable crosslinker can have a structure:

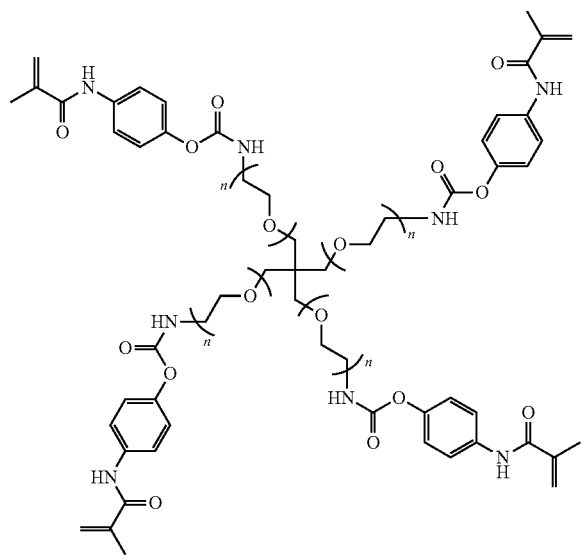

wherein each n is independently 1-20.

In another embodiment, a biodegradable crosslinker can have a structure:

The crosslinker(s) described herein can have a concentration less than about 5% w/w, less than about 4% w/w, less than about 3% w/w, less than about 2% w/w, less than about 1% w/w, or less than about 0.5% w/w of the prepolymer solution.

In some embodiments, in order to polymerize the monomers/macromers/crosslinkers, all the components of the polymer have moieties conducive to a polymerization reaction. A preferred polymerization mechanism can be free radical polymerization. If free radical polymerization is utilized to prepare the hydrogel filaments, all components have ethylenically unsaturated moieties. Functionalities for free radical polymerization can include acrylates, methacrylates, vinyl groups, and derivatives thereof. In one embodiment, functional groups of the monomers/macromers/crosslinkers are acrylates and/or methacrylates.

Alternatively, in other embodiments, other reactive chemistries can be utilized for the polymers. Other reactive chemistries can be nucleophile/N-hydroxysuccinimide esters, vinyl sulfone/acrylate, thiol-ene, or maleimide/acrylate.

In some embodiments, the polymer can be designed to dissolve in vivo, or biodegrade. Linkages unstable in the physiological environment, and therefore biodegradable, can be introduced to the macromer or crosslinker to impart biodegradation by hydrolytic, oxidative, or reductive mechanisms. Linkages susceptible to breakage in a physiological environment include those susceptible to hydrolysis, including esters, thioesters, carbamates, oxalates, and carbonates, and those susceptible to enzymatic action, including peptides that are cleaved by matrix metalloproteinases, collagenases, elastases, and cathepsins.

Multiple crosslinkers can be utilized to control the rate of degradation in a manner that is not possible with only one. In some embodiments, a multiple stage degradation can be achieved with differing crosslinkers. For example, crosslinkers with different degradation rates or modalities can be combined to provide a multimodal degradation pattern. A rapid initial degradation can could be achieved by using a rapid degrading crosslinker. A second slower degradation can be achieved by using a slow degrading crosslinker.

Polymer filaments containing pharmaceutical agents can be made to be visible using medically relevant imaging techniques such as fluoroscopy, computed tomography, or magnetic resonant imaging to permit intravascular delivery and follow-up. Visualization of the polymer filaments under fluoroscopy can be imparted by incorporating solid particles of radiopaque materials such as barium, bismuth, tantalum, platinum, gold, and other dense metals into the polymer or by polymerizing iodine-containing molecules into the polymer filament. Visualization agents for fluoroscopy can include barium sulfate and iodine-containing molecules.

In other embodiments, polymer visualization under computed tomography imaging can be imparted by incorporation of solid particles of barium or bismuth or by the incorporation of iodine-containing molecules polymerized into the polymer structure of the filament.

Metals visible under fluoroscopy can sometimes result in beam hardening artifacts that may preclude the usefulness of computed tomography imaging for medical purposes.

If used as a visualization agent to render the polymer visible using fluoroscopic and computed tomography imaging, barium sulfate can be present at a concentration of about 20% w/w, about 30% w/w, about 40% w/w, about 50% w/w, about 60% w/w, about 70% w/w, at least about 20% w/w, between about 30% w/w and about 60% w/w, between about 20% w/w and about 70% w/w, or between about 40% w/w and about 50% w/w of the prepolymer solution.

In some embodiments, the polymer can be visualized using fluoroscopic and computed tomography imaging when it includes about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, at least about 100 mg, at least about 125 mg, at least about 150 mg, between about 100 mg and about 500 mg, between about 125 mg and about 300 mg, or between about 100 mg and about 300 mg of iodine per gram of polymer.

Visualization of the filaments under magnetic resonance imaging can be imparted by incorporation of solid particles of superparamagnetic iron oxide or gadolinium molecules polymerized into the polymer structure. In one embodiment, a preferred visualization agent for magnetic resonance is superparamagnetic iron oxide. The particle size of the solid particles can be about 5 µm, about 10 µm, about 15 µm, about 20 µm, about 25 µm, between about 10 µm and about 25 µm, or between about 5 µm and about 15 µm. Concentrations of superparamagnetic iron oxide particles to render the hydrogel visible using magnetic resonance imaging range from 0.1% to 1% w/w of the prepolymer solution.

Pharmaceutical agents can be incorporated into the polymer filaments described herein in many different ways. Pharmaceutical agents can be any compound or drug having a therapeutic effect in an animal such as but not limited to active agents, drugs, therapeutic agents, and the like. Pharmaceutical agents can be in an active or inactive form when introduced into the filaments or when delivered. Pharmaceutical agents can include, but are not limited to anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

In a first method of incorporation, the pharmaceutical agent(s) can be entrapped in the polymer structure of the polymer filament. In one embodiment, the pharmaceutical agent is dissolved in the prepolymer solution and then it is entrapped in the network of the polymer as it is polymerized and formed as a filament. Once the filament is delivered to the diseased or otherwise desired site, the pharmaceutical agent diffuses out of the polymer filament. Advantages of this embodiment can include simplicity and being able to incorporate a wide variety of pharmaceutical agents into the polymer filaments. In some embodiments, it may necessary to match the solubility of the polymer components and the pharmaceutical agent(s).

Secondly, the pharmaceutical agent(s) can be loaded into the polymer. In this embodiment, monomers/macromers/crosslinkers are incorporated into the polymer network that can bind the desired pharmaceutical agent. While any binding mechanism can be used, a preferred binding mechanism is electrostatic interaction. In one embodiment, a monomer with an ionizable functional group that is basic (e.g. amines, derivatives thereof, or combinations thereof) can be incorporated into the polymer. The amine group is protonated at pH's less than the pKa of the amine, and deprotonated at pH's greater than the pKa of the amine. The incorporation of amine groups into the polymer can permit the incorporation of negatively charged pharmaceutical agents through electrostatic interaction.

In another embodiment, a monomer with an ionizable functional group that is acidic (e.g. carboxylic acids, sulfonic acids, phosphoric acids, derivatives thereof, or combinations thereof) can be incorporated into the polymer network. The acid group is deprotonated at pH's greater than the pKa of the acid, and protonated at pH's less than the pKa of the acid. The incorporation of acidic groups into the polymer can permit the incorporation of positively charged pharmaceutical agents through electrostatic interaction.

After the preparation and washing of the polymer filament, the pharmaceutical agent is dissolved into a suitable aqueous solvent and the polymer filament is placed in that solution. The pharmaceutical agent is loaded into the polymer filament. Once the polymer filament is delivered to the diseased site, the pharmaceutical agent is released by exchange with other counter ions readily available in the physiological environment and diffuses out of the polymer filament. The advantages of this embodiment include simplicity, the ability to wash the polymer filament before loading with the pharmaceutical agent, and potentially higher loadings of pharmaceutical agents.

In a third way, the pharmaceutical agent(s) can be incorporated into the polymer filament. In this embodiment, the pharmaceutical agent is chemically modified to permit incorporation into the network of the filament and to permit decoupling from the polymer in a controlled rate at the diseased site. The incorporation can be achieved by adding a moiety amenable to the polymerization mechanism selected for the polymer. The modification turns the pharmaceutical agent into a monomer. The decoupling is achieved by adding a linkage unstable in a physiological environment between the polymerization group and the active agent. This linkage can break via hydrolytic, oxidative, or reductive mechanisms available in the physiological environment. Linkages susceptible to breakage in a physiological environment include those susceptible to hydrolysis, including esters, thioesters, carbamates, oxalates, and carbonates, and those susceptible to enzymatic action, including peptides that are cleaved by matrix metalloproteinases, collagenases, elastases, and cathepsins. Multiple decoupling linkages can be used to control the rate of release of the pharmaceutical agent in a manner that is not possible with only one, i.e. one linkage to permit a large, rapid release immediately following implantation and another linkage to permit a slow, sustained release over longer periods of time. After preparation of polymers with incorporated active agents, extensive washing of the polymers may not prematurely release the pharmaceutical agent. Once the polymer is delivered to the diseased site, the pharmaceutical agent decouples from the polymer as the linkage breaks and diffuses into the diseased site. Advantages of this embodiment include the ability to wash the polymer filament before loading with pharmaceutical agent, highest loadings of pharmaceutical agents, complete control of the release kinetics, and suitability of the widest range of pharmaceutical agents.

In some embodiments, pharmaceutical agents can be polymerizable pharmaceutical agents. In one embodiment, polymerizable pharmaceutical agents or pharmaceutical agents amenable to polymerization can have a structure

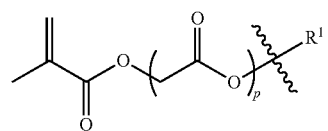

wherein $R^1$ is a pharmaceutical agent; and
is 0, 1, 2, 3 or 4.

For example, in some embodiments, $R^1$ can have a structure

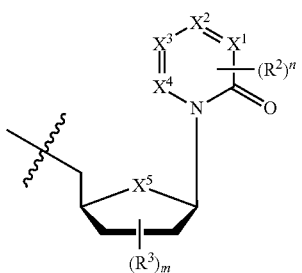

wherein each $R^2$ and $R^3$ can independently be H, $CH_3$, $C_2$-$C_6$ alkyl, $C_2$-$C_6$ substituted with a halogen or other $C_1$-$C_6$ alkyl, $NH_2$, $CO_2$, CN, $CF_3$, F, Cl, Br, I, $CCl_3$, OH, or $CH_2OH$;
n is 1, 2, 3, or 4;
m is 1, 2, 3, or 4;
$X^1$, $X^2$, $X^3$, and $X^4$ are each N or CH; and
$X^5$ is O, $CH_2$, or NH.

In another embodiment, $R^1$ has a structure

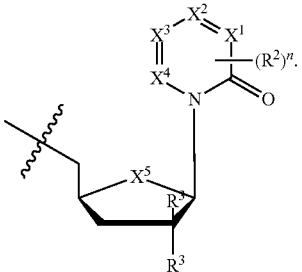

In still another embodiment, $R^1$ has a structure

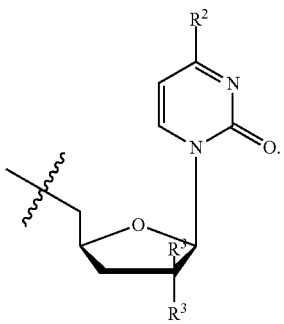

In one embodiment, $R^1$ has a structure

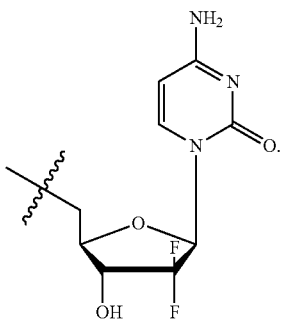

In one embodiment, the pharmaceutical agent amenable to polymerization has a structure

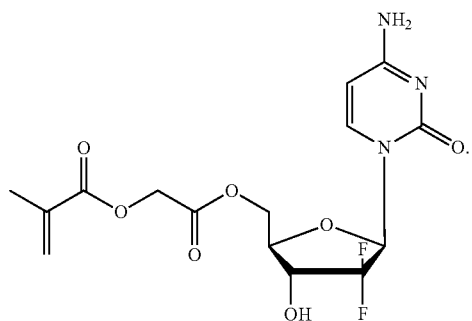

In another embodiment, a pharmaceutical agent amenable to polymerization has a structure

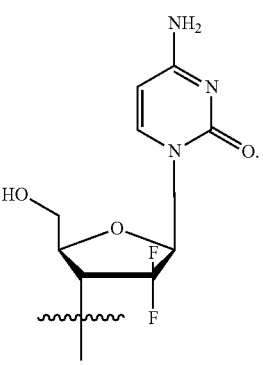

In another embodiment, a pharmaceutical agent amenable to polymerization has a structure

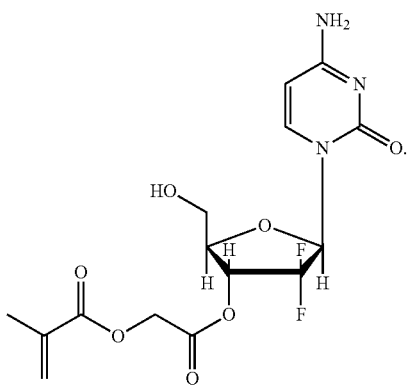

In some embodiments, a combination of pharmaceutical agent amenable to polymerization can be used. In such an embodiment, combination of

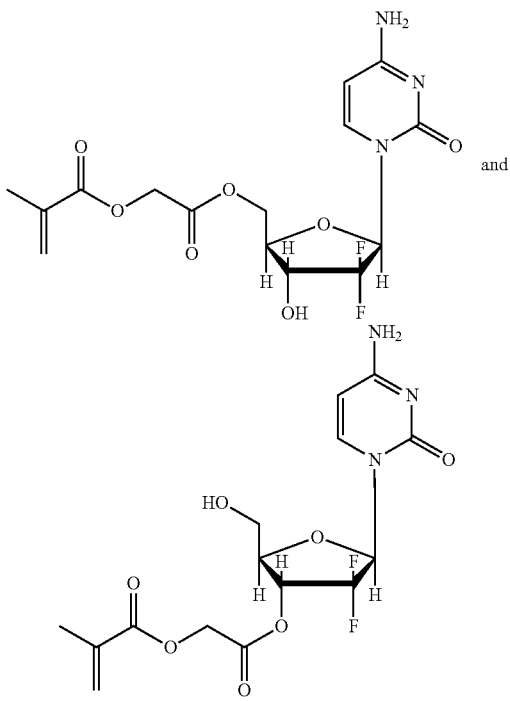

can be used. Combination ratios can be about 1:99, about 10:90, about 20:80, about 30:70, about 40:60, about 50:50, about 60:40, about 70:30, about 80:20, about 90:10, or about 99:1.

In another embodiment, a pharmaceutical agent amenable to polymerization has a structure

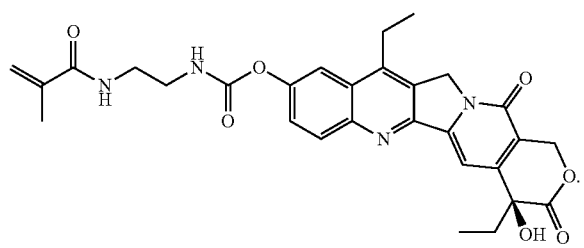 [SMILES: C=C(C)C(=O)NCCNC(=O)Oc1ccc2nc3c(c(CC)c2c1)Cn1c-3cc2c(c1=O)COC(=O)[C@]2(O)CC]

In another embodiment, a pharmaceutical agent amenable to polymerization has a structure

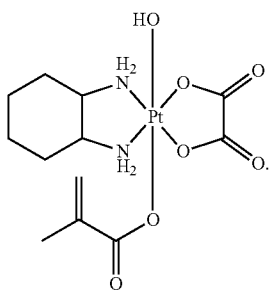

Also, various combinations of the above listed pharmaceutical agents can be used with filaments as described herein.

Methods of forming the polymer filaments are also described. Methods of forming therapeutic polymer filaments or other elongated structures can comprise: reacting a prepolymer solution. The prepolymer solution can include at least one macromer, at least one visualization agent, and a pharmaceutical agent physically entrapped in the polymer filament, electrostatically bound to the polymer filament or chemically bound to the polymer matrix.

In another embodiment, the prepolymer solution can include (i) one or more macromers and (ii) one or more pharmaceutical agents. In another embodiment, the prepolymer solution can include (i) one or more monomers, one or more macromers, and/or one or more crosslinkers, and (ii) one or more pharmaceutical agents. In still another embodiment, the prepolymer solution can include (i) one or more crosslinkers and (ii) one or more pharmaceutical agents.

The prepolymer solution can optionally include (iii) one or more visualization agents. Different combinations of monomers/macromers/crosslinkers can provide differing physical properties for the resulting polymers. Different polymeric physical properties can include, but are not limited to tensile strength, elasticity, and/or delivery through a microcatheter or catheter. The resulting polymers and/or polymer filaments can include one or more pharmaceutical agents physically entrapped in the polymer filament, electrostatically bound to the polymer filament or chemically bound to the at least one monomer.

The resulting polymer filament can be prepared for implantation. After formation, the polymer filament can be loaded into a support member. The support member can be formed of a metal. In other embodiments, the support member is not formed of a metal, but rather formed of a material such as a plastic or other polymer. In other embodiments, the polymer filaments do not require any support members to be delivered.

For example, to prepare a polymer such as in the shape or form of a filament or other elongated structure, a tubular extrusion is filled with prepolymer solution. The extrusion is the mold for the filament. In some embodiments, if one of the components is solid, a solvent will be utilized in the preparation of the filaments. If liquid components are utilized, a solvent may not be required, but may be desired. Any aqueous or organic solvent may be utilized that fully dissolves the desired monomers/macromers/crosslinkers, soluble visualization agents, pharmaceutical agents, and polymerization initiators may be used. Solvents can include but are not limited to water, methanol, ethanol, isopropyl alcohol, ether, dimethylformamide, and the like. Solvent concentrations can be about 10% w/w, 20% w/w, 30% w/w, 40% w/w, 50% w/w, 60% w/w, 70% w/w, 80% w/w, between about 20% w/w and about 80% w/w, between about 20% w/w and about 50% w/w, or between about 40% w/w and about 80% w/w. In one embodiment, the solvent is dimethylformamide.

The prepolymer solution can be polymerized by reduction-oxidation, radiation, heat, or any other method known. Radiation cross-linking of the prepolymer solution can be achieved with ultraviolet light or visible light with suitable initiators or ionizing radiation (e.g. electron beam or gamma ray) without initiators. Cross-linking can be achieved by application of heat, either by conventionally heating the solution using a heat source such as a heating well, or by application of infrared light to the monomer or prepolymer solution.

Free radical polymerization of the prepolymer solution in some embodiments is preferred and may require an initiator to start the reaction. In a preferred embodiment, the cross-linking method utilizes azobisisobutyronitrile (AIBN) or another water soluble AIBN derivative (2,2'-azobis(2-methylpropionamidine)dihydrochloride). Other useful initiators can include N,N,N',N'-tetramethylethylenediamine, ammonium persulfate, benzoyl peroxides, and combinations thereof, including azobisisobutyronitriles. Initiator concentrations can be about 1% w/w, about 2% w/w, about 3% w/w, about 4% w/w, about 5% w/w, between about 0.5% w/w and about 5% w/w, between about 1% w/w and about 3% w/w, or between about 2% w/w and about 3% w/w. In one embodiment, azobisisobutyronitrile is used as an initiator.

In some embodiments, the prepolymer solution is prepared by placing the monomer/macromer/crosslinker, visualization agent, pharmaceutical agent, and initiator in the solvent. After dissolution of these components, an insoluble visualization agent, such as barium sulfate or superparamagnetic iron oxide particles, can be suspended in the prepolymer solution. In other embodiments, this insoluble visualization agent is not used. Mixing of the prepolymer solution containing an insoluble visualization agent with a homogenizer can aid the suspension of the insoluble visualization agent.

The prepolymer solution can then be injected into tubing with an inner diameter ranging from 0.015 cm to 0.19 cm and incubated for several hours at elevated temperature or in boiling water, i.e. 100° C., and subsequently overnight at 80° C. to complete polymerization. Immersion in boiling water allows for rapid heat transfer from the water to the prepolymer solution contained in the tubing.

The selection of the tubing imparts micro catheter or catheter compatibility. For delivery through microcatheters, tubing diameters from about 0.006 in to about 0.025 in can be used. In one embodiment, the tubing is made from HYTREL® (DuPont, Wilmington, Del.). The HYTREL® tubing can be dissolved in solvents, facilitating removal of a polymer filament from the tubing.

If the tubing is wrapped around a mandrel prior to polymerization of the prepolymer solution, the resulting hydrogel filament maintains the shape of the wrapped tubing. Using this wrapping technique, helical, tornado, and complex shapes can be imparted to the finalized filaments. When the tubing is wrapped around a mandrel, the use of oval tubing may be preferred. After wrapping around the mandrel, the oval shape of the tubing is rounded and the resulting hydrogel filament has a round shape in the coiled configuration.

If HYTREL® tubing is utilized, the hydrogel filament can be recovered by incubating the tubing in a solution of 20% w/w phenol in chloroform followed by washing in chloroform and ethanol. After the filament is washed, it is dried.

Filaments or other elongates structures formed using the present methods can vary in length depending on the method parameters used. However, generally, filament lengths can range from about 0.5 cm to about 100 cm, about 1 cm to about 50 cm, about 10 cm to about 100 cm, or about 0.5 cm to about 25 cm. Likewise diameters can vary. For example, diameters can be about 0.010 cm to about 0.50 cm, about 0.015 cm to about 0.19 cm, or about 0.010 cm to about 0.20 cm.

After recovery and washing of the filament, it is fabricated into a device suitable for use by a physician, surgeon, or other practitioner. If a repositionable device is desired, a length of filament is inserted into a tube slightly larger than the filament's diameter. This straightens the secondary shape of the filament and permits the gluing of a poly(ether-ether-ketone) coupler to one end of the filament. Subsequently the coupler is attached to a pusher, packaged, and sterilized.

Upon receipt, the physician introduces the filament into a microcatheter or catheter and then pushes it through the microcatheter or catheter to an embolization or other medically relevant site. The filament can be advanced and withdrawn until the physician is satisfied with its position. Then the filament can be detached from the pusher.

If a pushable device is desired, a dried hydrogel filament is loaded into an introducer, packaged in a suitable pouch, and sterilized. Upon receipt, the physician transfers the hydrogel from the introducer to a microcatheter or catheter using a guide wire or stylet. The dried filament is then pushed through the microcatheter or catheter and into an embolization site or other medically relevant site using a guide wire.

Example 1

Preparation of a Hydrogel Filament with Entrapped Pharmaceutical Agent

To prepare a hydrogel filament with entrapped active pharmaceutical agent, 2.25 g of trimethylolpropane triacrylamide, 1.25 g of barium sulfate and 0.2 g of gemcitabine hydrochloride were added to 2.5 g of water. The solution was sparged with argon for 10 min. To initiate polymerization, 20 µL of tetramethylethylenediamine and 12 µL of a 20% solution of ammonium persulfate in water was added just before injection into 0.045 inch ID polyethylene tubing using a 1 cc syringe. The tubing was heat sealed at both ends and allowed to polymerize overnight at room temperature.

Once polymerized, the tubing was cut into 15 cm sections and placed in a vacuum oven to remove any residual water. Once dry, the hydrogel filaments were pushed out of their tubes using a mandrel. The gemcitabine-containing hydrogel filaments were washed in ethanol for 2 hr to remove any unreacted components, then dried overnight in a vacuum oven.

Example 2

Preparation of a Degradable Radiopaque Monomer

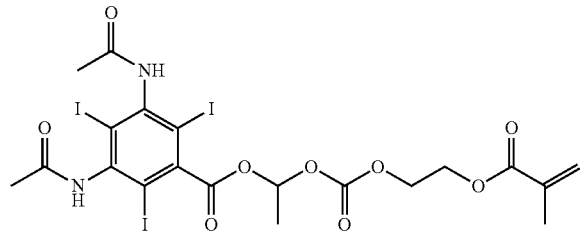 [SMILES: C=C(C)C(=O)OCCOC(=O)OC(C)OC(=O)c1c(I)c(NC(C)=O)c(I)c(NC(C)=O)c1I]

To 400 mL of methanol was added 104 g (170 mmol) of diatrizoic acid followed by 28 g of cesium carbonate (65 mmol). After stirring for 45 min the methanol was removed in vacuo and the solids suspended in 500 mL of diethyl ether. The solids were then collected and dried on a Buchner funnel and further dried in vacuo, to yield 120 g, (95%) (Cesium Diatriozate, 1).

To 24 mL of HEMA (200 mmol) in 1,000 mL of dry ether was added 16.8 mL (213 mmol) of pyridine at 4-10° C., under Ar. To this solution was added 21.3 mL (200 mmol) of 1-chloroethyl chlorocarbonate, drop wise with stirring over 0.5 hr. After stirring 0.5 hr at 4-10° C., the heavy precipitate was removed by filtration and the filtrate was concentrated to oil in vacuo, yielding 44 g (100%) (HEMA-1-Chloroethyl carbonate, 2).

To 44 g (200 mmol) of (2) in 400 mL of anhydrous DMF was added 30 g (40 mmol) of (1) at 100° C. under Ar, with good stirring. After 15 min another 40 g (54 mmol) of (1) was added at 100° C., under Ar, with good stirring followed by a final 30 g (40 mmol), under the same conditions, for a total of 110 g (1) (134 mmol). The reddish brown reaction mixture was heated at 100° C. for an additional hour and the solvent was removed in vacuo. The reddish brown solid residue was suspended in 1,000 mL of dry ether and the solids were collected on a Buchner funnel. After the solids were dried in vacuo, they were suspended in 500 mL distilled water at 2,000 rpm and the mixture pH was adjusted to 8-9 with cesium carbonate. After stirring for 10 min, the suspension was filtered and the solids were washed 3 times with 100 mL of distilled water, dried overnight in vacuo and crushed to a fine powder. Solid residue was again suspended in 1,000 mL of dry ether and the solids were collected on a Buchner funnel. After the solids were dried in vacuo again and crushed to a fine powder again, they were purified by silica gel chromatograph using a 1.5 Kg column and a 0-10% gradient of methanol in dichloromethane, over 1 hr. This yielded 26 grams (18%), very pale yellow crystalline solid (1-((. 2-(methacryloyloxy)ethoxy)carbonyloxy)ethyl-3,5-diacetam ido-2,4,6-triiodobenzoate, 3).

Example 3

Preparation of a Non-Degradable Radiopaque Monomer

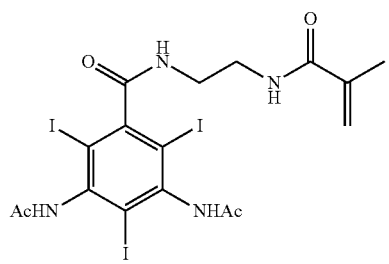 [SMILES: C=C(C)C(=O)NCCNC(=O)c1c(I)c(NC(C)=O)c(I)c(NC(C)=O)c1I]

Diatriazoyl Acetate (A): To 30.8 g of diatrizoic acid suspended in 100 mL of acetic anhydride was added 2 g of concentrated sulfuric acid and the resulting suspension stirred at 90 degrees centigrade for one hour before the reaction mixture was cooled to room temperature and then poured onto 500 g of ice. After agitating the ice for 15 min, the oily mass was treated with 100 mL of half saturated sodium bicarbonate whilst agitating. The solids which had formed were collected on a Buchner funnel and dried overnight in vacuo to give 9 g of light brown diatriazoyl acetate solids.

Diatriazoyl Chloride (B): Nine grams of ditriazoyl acetate was suspended in 100 mL of thionyl chloride using overhead stirring. The reaction mixture was brought to reflux in an oil bath and refluxed for one hour. The thionyl chloride was mostly removed in vacuo at 40° C. at which point solids were re-suspended in 100 mL of ethyl acetate which was removed in vacuo. This process was repeated twice more at which point the solids were placed under vacuum overnight.

Ethylenediamine mono-diatriazoyl amide (C): 6.3 g of the acid chloride (10 mmol) in 300 mL of methylene chloride was added to 6.7 grams of ethylene diamine (100 mmol) over one hour with stirring at 4-10° C. under Ar. The formed solids were collected on a Buchner funnel and washed with 100 mL of methylene chloride and dried overnight in vacuo. The dried solids now largely free of ethylenediamine were taken up in 600 mL of water filtered through a fritted disk funnel and the water removed in vacuo. The residue was triturated with acetonitrile which was then evaporated in vacuo to remove traces of water. LC-MS showed 640 which is $(M+Na)^+$ and 656.9, $(M+K)^+$.

Ethylene diamine-1-diatriazoylamide-2-methacrylamide (D): To 650 mg of (C) (1 mmol) suspended in 100 mL of $THF/CHCl_3$/ethanol, 1/3/1 was added 0.18 mL (1.04 mmol) of diisopropylethylamine followed by 0.12 mL (1.26 mmol) of methacryoyl chloride with stirring under Ar. The reaction mixture was stirred for 1 hr at which point reaction mixture was filtered with a fritted Buchner funnel.

TLC with 10% methanol in methylene chloride showed potential product in solids and filtrate. LC-MS of combined filtrate and solids after solvent removal in vacuo showed $(M+H)^+$ at 725.0, $(M+Na)^+$ at 747.0 as well as $(M-H)^-$ at 723.0 and $(M+Na-2H)^-$ at 744.9 all on an HPLC peak at 8.9 min in a 15 min run.

Example 4

Preparation of a Degradable Radiopaque Monomer

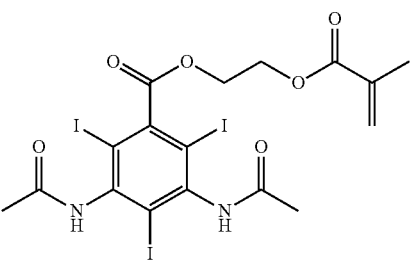 [SMILES: C=C(C)C(=O)OCCOC(=O)c1c(I)c(NC(C)=O)c(I)c(NC(C)=O)c1I]

Tetrabutylammonium diatrizoate: To a stirring suspension of diatrizoic acid (50 g, 81.4 mmol) in methanol (552 mL) was slowly added tetrabutylammonium hydroxide (40% aqueous solution, 52.8 mL). The turbid suspension turned clear after the addition of tetrabutylammonium hydroxide was finished. The solvent was removed using a rotary evaporator to obtain a cream-colored viscous residue. To this residue was added appropriate amount of toluene, which was then removed using a rotary evaporator. Toluene was added to the residue once more and removed again. The solid obtained was dried in a vacuum oven overnight at 40° C. to afford a white solid (64.1 g, 92% yield).

Diatrizoyl HEMA: To a stirring solution of KI (796.8 mg, 4.38 mmol) and 2-chloro ethylmethacrylate (4.32 mL, 32.1 mmol) in anhydrous DMF (122.6 mL) was added tetrabutylammonium diatrizoate (25 g, 29.2 mmol) under argon. The flask was place in a 60° C. oil bath. Additional KI (199 mg) and 2-chloro ethylmethacrylate (1 mL) was added to the reaction at 13 hours, 38 hours and 41 hours reaction times. The reaction was pulled out of the oil bath at 44 hours and cooled under room temperature. The reaction was poured over saturated NaHCO$_3$ aqueous solution (120 mL) and a white precipitate formed. The aqueous phase was extracted once with a mixture of ethyl acetate (280 mL) and methanol (50 mL). The organic phase was washed with saturated sodium chloride aqueous solution (300 mL×1). The organic phase was subjected to rotary evaporation to obtain a cream-colored wet solid. The solid was suspended in a mixture of methyl tert-butyl ether and chloroform (7:3, v/v), and the resulting suspension was filtered to obtain a white solid. The solid dried under reduced pressure to obtain the first crop of product as a white solid (11.898 g). The previous NaHCO$_3$ phase was filtered and a white solid was collected. The solid was washed with a mixture of methyl tert-butyl ether and chloroform (7:3, v/v) and dried under reduced pressure to afford the second crop (3.071 g). The first and second crops were combined to afford the final product as a white solid (14.969 g, 70.6% yield).

Example 5

Preparation of a Biodegradable Crosslinker

To 10 g (67.6 1 mnol) of 2,2'-ethylenedioxy-bis-ethylamine was added 10 g (70.4 mmol) of glycidyl methacrylate and 3.0 g of silica gel (Aldrich 645524, 60 Angstrom 200-425 mesh), with good stirring. After stirring for 1 hr, another 9 g (63.4 mmol) of glycidyl methacrylate was added and the suspension was stirred for an additional 1.5 hr. The reaction mixture was diluted with 200 mL of reagent grade chloroform and filtered through a 600 mL fritted glass Buchner funnel of medium porosity, to remove silica gel. LC-MS analysis of the resultant chloroform solution showed almost no mono-glycidyl amino alcohol and mostly bis-glycidyl amino alcohol at (M+H)$^+$ 433.2 and was concentrated to about 50 g in vacuo. The resultant heavy syrup was diluted to 100 mL with acetonitrile and stored at −80° C.

Example 6

Preparation of a Biodegradable Crosslinker

TMP-Chloroacetamide (E): To 13.2 g of TMP amine in 250 mL of dry THF was added 6.32 g (80 mmol) of pyridine and this solution was added to 6.44 g of chloroacetyl chloride in 250 mL of THF with good stirring, at 4-1° C. under Ar. After stirring for 15 min, the reaction mixture was warmed to room temperature and the THF and other volatile materials were removed in vacuo. The resulting solids were dissolved into 200 mL of chloroform, washed with 100 mL of saturated aqueous sodium bicarbonate, dried over magnesium sulfate, and the solvent was removed in vacuo.

TMP-NH-Gly-Methacrylate (F): Approximately 15 grams of (E) was dissolved into 75 mL of anhydrous DMF and added 18 g of cesium methacrylate was added. The resulting suspension was heated at 40-50° C. for 2 hr.

After precipitation with 500 mL of chloroform, the inorganic salts were collected by filtration and the filtrate was concentrated in vacuo to give 18 g of a reddish brown oil. This oil was polymerized with AIBN at 80° C., in isopropyl alcohol to a nice hard pellet. Chromatography on 6 g of this through a plug of silica with 1,200 mL of 2-20% methanol in chloroform, gave 6 g of light red colored material. This material can be used to prepare polymer filaments.

The material can have a structure

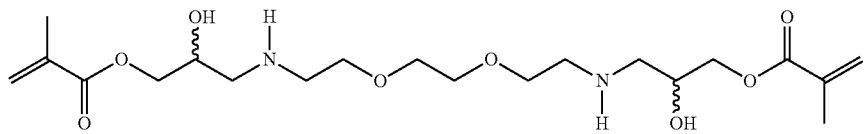

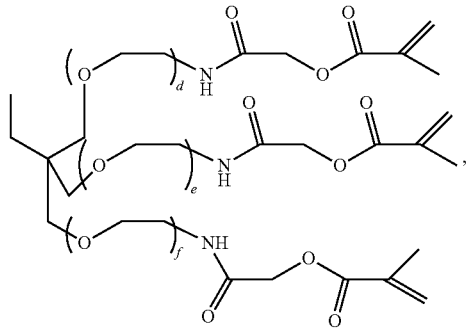

wherein d, e, f, and g are each independently 1-20.

Example 7

Preparation of a Biodeciradable Crosslinker

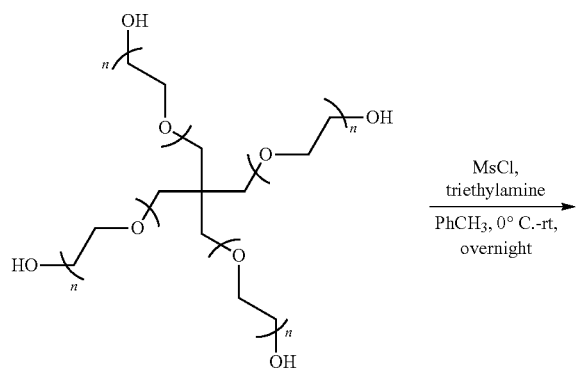

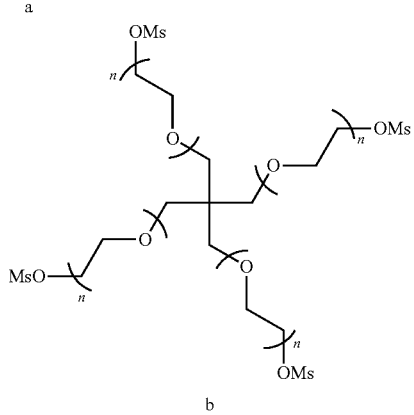

Preparation of tetramesyl pentaerythritol (b): To a 3 L three-neck round bottom flask fitted with a Dean-Stark trap was added pentaerythritol (a, MW~797 g/mol, 99.9 g, 125 mmol) and toluene (1.5 L) sequentially. The solution was subjected to an azeotrope distillation and water was removed from the Dean-Stark trap. The flask was cooled to room temperature before triethylamine (94.6 mL, 530 mmol) was added. Then the flask was placed in a 0° C. ice bath. A 250 mL addition funnel was attached to the flask. To the addition funnel was added anhydrous toluene (80 mL) and mesyl chloride (40 mL, 530 mmol) sequentially. The mesyl chloride solution wad added dropwise to the cooled solution. The reaction was left to stir at room temperature overnight, resulting in the formation of a white precipitate. At the end of the reaction, the solution was filtered over a fritted glass funnel to remove the precipitate. The filtrate was concentrated using a rotary evaporator to afford the crude material as a pale yellow oil (86.37 g).

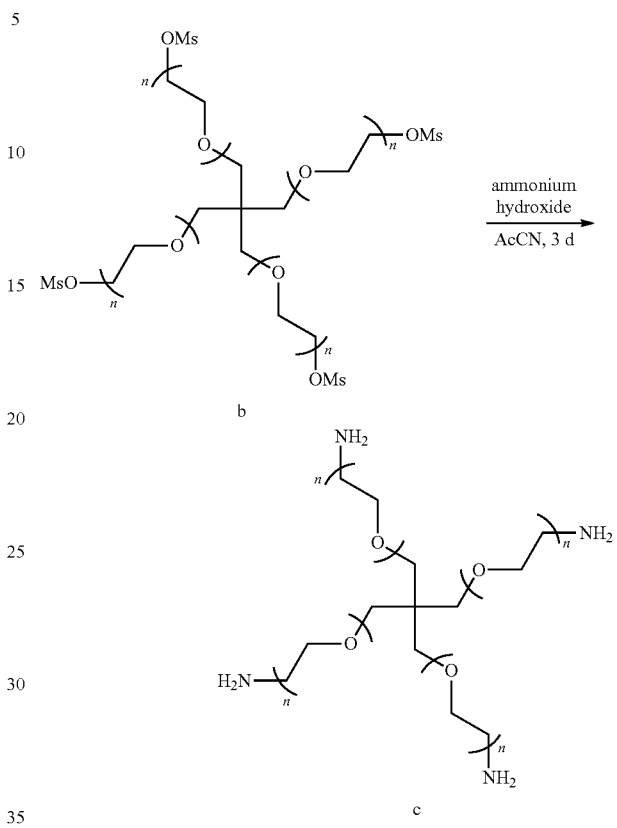

Preparation of tetraamino pentaerythritol (c): To a solution of ammonium hydroxide (30%, 1250 mL, 22.02 mol) was added dropwise tetramesyl pentaeryhtriol (b, 86.37 g, 77.8 mmol) in anhydrous acetonitrile (500 mL). The reaction was stirred under room temperature for three days. Upon completion, it was degassed for 2 days using an air pump. Then the pH of the residue was adjusted to 14 using 0.1 M NaOH aqueous solution. The aqueous phase was extracted with dichloromethane (500 mL×1, and 1 L×1). The organic phase was then dried over sodium sulfate and concentrated using a rotary evaporator to afford the product as a pale yellow oil (56.31 g).

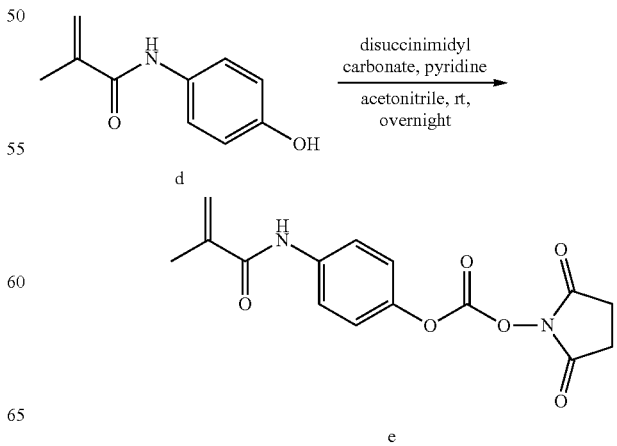

23

Preparation of NHS-activated (4-hydroxyphenylmethacrylamide) (e): To a solution of (4-hydroxyphenylmethacrylamide) (d, 20 g, 113 mmol) in anhydrous acetonitrile (78.8 mL) was added anhydrous pyridine (9.12 mL, 113 mmol) and disuccinimidyl carbonate (72.4 g, 283 mmol) sequentially. The solution was stirred for 18 hours at room temperature. Then the reaction was poured over dichloromethane (80 mL) and filtered over a Buchner funnel. The filtrate was washed with 2.5% aqueous copper sulfate solution (100 mL×1), and then saturated sodium chloride solution (100 mL×1). It was dried over sodium sulfate and concentrated under reduced pressure. The residue was passed through a short silica gel plug before being separated on flash chromatography using a gradient of ethyl acetate and dichloromethane. The product is a cream-colored solid (3.71 g, yield: 10.3%).

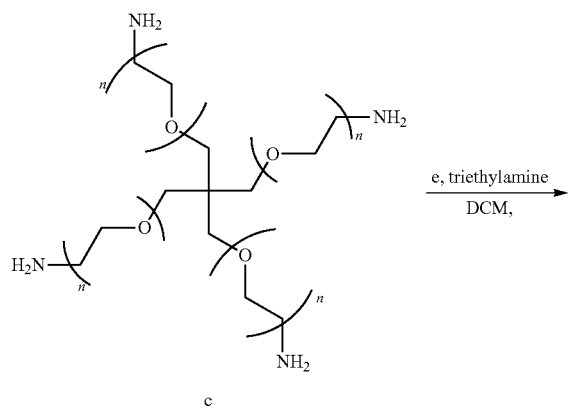

c

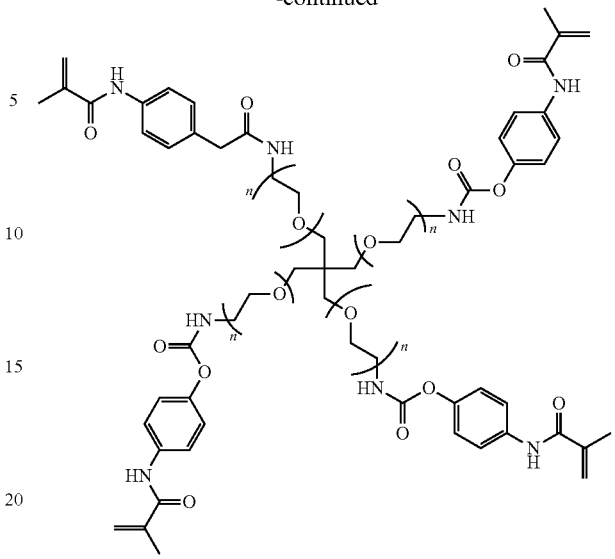

f

Preparation of a biodegradable crosslinker (f): To a solution of tetraamino pentaerythritol (c, 10.0 g, 12.6 mmol) and trimethylamine (7.0 mL, 50.4 mmol) in dichloromethane (67 mL) was added NHS-activated (4-hydroxyphenylmethacrylamide) (e, 16.0 g, 50.4 mmol) under argon. The solution was stirred for 3 hours 15 minutes. Upon completion, it was passed through a silica gel plug. The elution was using a rotary evaporator, and the residue was separated using flash chromatography to afford the product.

Example 8

Preparation of a Biodeciradable Crosslinker

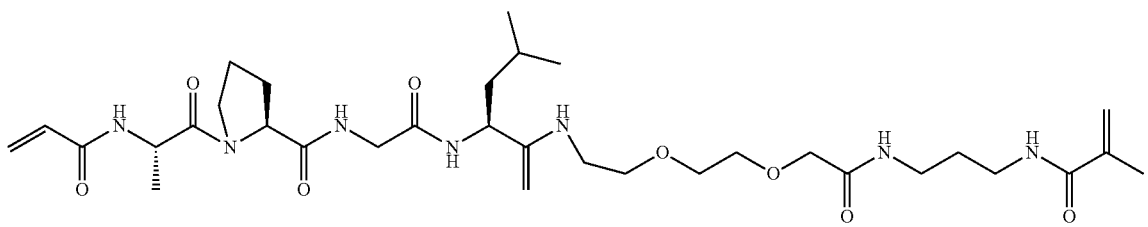 [SMILES: C=CC(=O)N[C@@H](C)C(=O)N1CCC[C@H]1C(=O)NCC(=O)N[C@@H](CC(C)C)C(=C)NCCOCCOCC(=O)NCCCNC(=O)C(=C)C]

To 653 mg (1 mmol) of tetrapeptide Alanine-Proline-Glycine-Leucine (APGL) in 5 mL dry DMF was added 190 mg (1.1 mmol) of APMA-HCl, followed by 174 µL (1 mmol) of DIPEA, at room temperature with good stirring, under Ar. After 2 hr, the reaction mixture was treated with 20 mg of BHT and briefly exposed to air. LC-MS analysis showed $(M+H)^+$ at 680 and $(M+Na)^+$ at 702. Then, 5 mL of the reaction mixture was added dropwise to 200 mL of ether with good stirring and the solids which formed were collected by centrifugation. The resulting pellet was dissolved into 20 mL of ($CHCl_3$/MeOH/MeOH+5% aqueous ammonia) 90/5/5, and applied to 50 g of silica gel in a 5×20 cm column (Aldrich 645524, 60 Angstrom 200-425 mesh). The silica gel column was developed with 500 mL of ($CHCl_3$/MeOH/MeOH with 5% aqueous ammonia), 90/5/5. The peptide containing eluent (TLC, same solvent) was concentrated in vacuo to yield 110 mg of pale yellow oil, LCMS, as above. The pale yellow oil was dissolved in 10 mL of methanol and stored at −80° C.

Example 9

Preparation of a Hydrogel Filament with Loaded Pharmaceutical Agent

A To prepare a filament loaded with a pharmaceutical agent, 1.34 g of sulfoethyl methacrylate, 0.66 g of the material described in Example 4, 0.1 g of pentaerythritol ethoxylate tetra-acrylate, and 0.025 g of azobisisobutyronitrile were dissolved in 3.4 g of dimethylformamide. The solution was sparged with Ar for 10 min before injection into 0.045 inch ID HYTREL® tubing using a 1 cc syringe. The tubes were heat sealed at both ends and placed in a 100° C. water bath for 1 hr, then overnight in an 80° C. oven to polymerize the solution.

The hydrogel was removed by dissolving the tubing in a solution of 20% phenol in chloroform. After the tubing was dissolved, the phenol solution was exchanged with chloroform and washed for 1 hr. After 1 hr, the chloroform was exchanged and the hydrogel washed for another 1 hr. The chloroform was removed and the hydrogel dried in a vacuum oven for 2 hr at 25° C. To remove any unreacted monomers, the hydrogel was placed in ethanol for 12 hr. After 12 hr, the ethanol was exchanged and washed for 2 hr. After 2 hr, the ethanol was exchanged and the hydrogel washed for another 2 hr. The ethanol was removed and hydrogel dried in vacuo for 12 hr. The hydrogel filaments were placed in a 10 mg/mL solution of gemcitabine in water adjusted to pH 4.5 using ammonium hydroxide to load. After 45 min, the filaments were placed in ethanol for 2 hr for desiccation. The filaments were then placed in a room temperature vacuum oven overnight to remove the ethanol.

Example 10

Preparation of a Polymerizable Pharmaceutical Agent

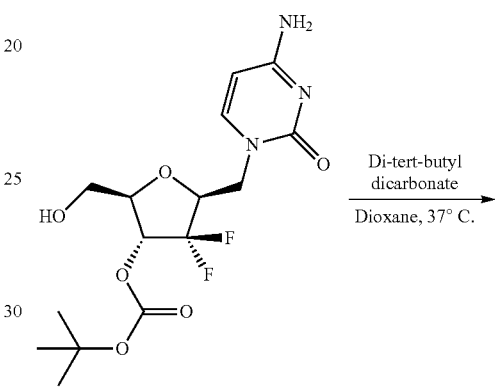

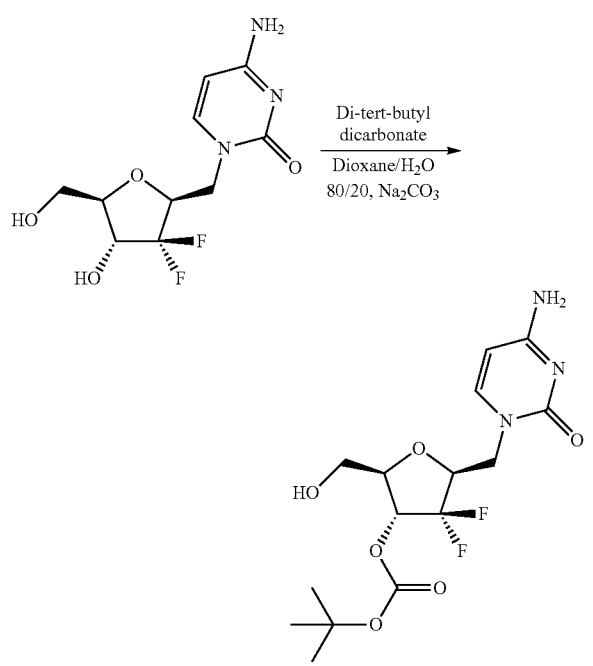

3'-O-(tert-Butoxycarbonyl)gemcitabine: To 3.0 g (10 mmol) gemcitabine in 200 mL of dioxane was added 2.2 g (10 mmol) of di-tert-butyl dicarbonate followed by 5.5 g of sodium carbonate and finally 50 mL of water, with good stirring under Ar. After stirring for 48 hr, the solvent was removed in vacuo and the residue distributed between 400 mL water and 1,000 mL of ethyl acetate. The aqueous layer was washed with an additional 500 mL of ethyl acetate, dried with sodium sulfate, and the solvent was removed in vacuo to give a colorless foam which was mostly one spot to TLC (50, 40, 10: $CH_2Cl_2$/acetone/ethanol), $R_f$ of about 0.4. LC-MS showed $(m+1)^+$ of 393.9. Silica gel chromatography on 4×30 cm column with 1:1:0.02-1:1:0.04, $CH_2Cl_2$/acetone/ethanol gave 2.1 g of material. The NMR of this compound was the same as previously reported. (Acetone-d6/$D_2O$).

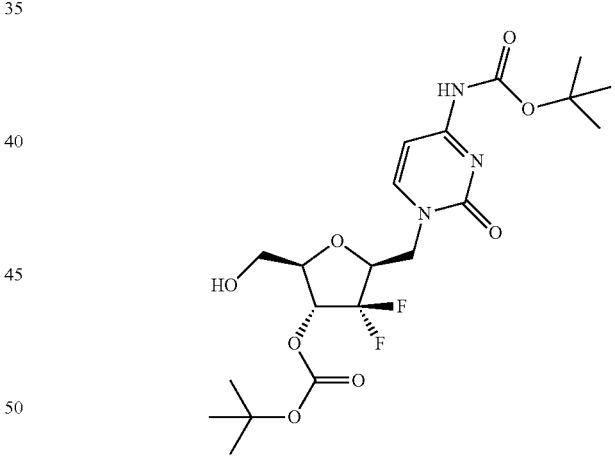

4-N-3'-O-Bis(tert-Butoxycarbonyl)gemcitabine: To 2.1 g (6 mmol) of 3'-O-(tert-butoxycarbonyl)gemcitabine in 200 mL of dioxane was added 13.2 grams of di-tert-butyl dicarbonate and the reaction mixture was placed in an oven at 37° C. for 72 hr. At the end of this time, the solvent was removed in vacuo and the residue was placed on the vacuum line at 10 micron for 0.5 hr. The solids which formed were dissolved in 40 mL of $CHCl_3$ and subjected to silica gel chromatography with a gradient of $CHCl_3$ to 10% acetone in $CHCl_3$, yielding 2.5 g of 4-N-3'-O-bis(tert-butoxycarbonyl) gemcitabine material whose NMR (Acetone-d6/$D_2O$) was consistent with the proposed structure.

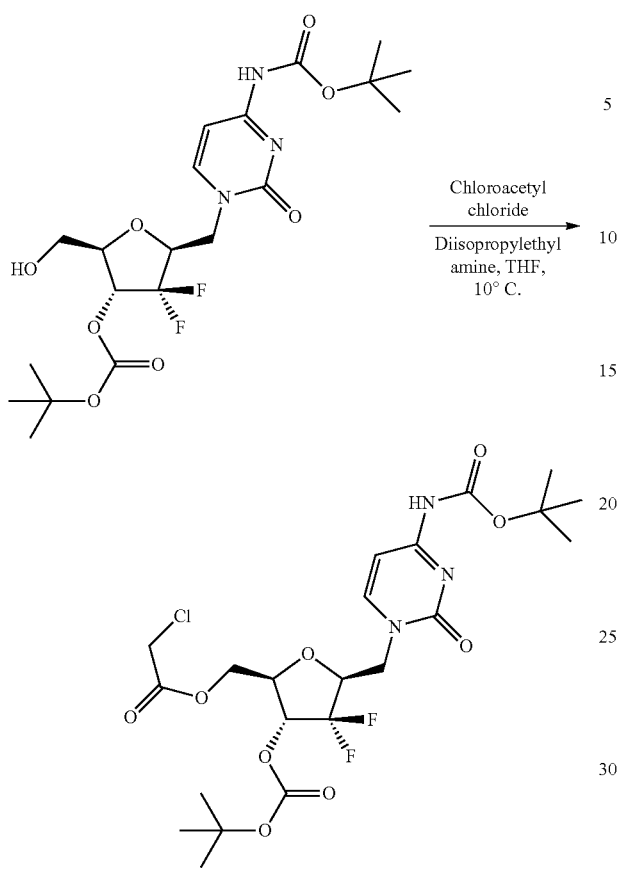

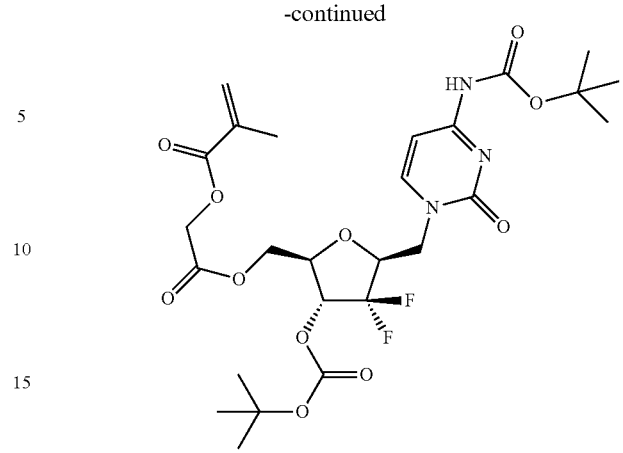

Methacryoyl-5'-O-glycolyl-4-N-3'-O-Bis(tert-butoxycarbonyl)Gemcitabine: Foamy semisolids of 5'-O-chloroacyl-4-N-3'-O-bis(tert-butoxycarbonyl)gemcitabine (taken as 2 mmol) were taken up into 30 mL of dry DMF and treated with 955 mg (4.3 mmol) of cesium methacrylate at 50-80° C. for 4 hr. Solvent was removed in vacuo and brown residual oil was taken up into 150 mL of ethyl acetate and washed with portions of saturated aqueous sodium bicarbonate, dried over sodium sulfate. After solvents were removed, the residue was subjected to silica gel chromatography with a gradient of 2:1 hexane/ethyl acetate to 3:2 hexane/ethyl acetate to give a brown semi-solid whose NMR (acetone-d6/D$_2$O) was consistent with the proposed structure.

5'-O-chloroacyl-4-N-3'-O-Bis(tert-Butoxycarbonyl)Gemcitabine: To 926 mg (2.01 mmol) of 4-N-3'-O-bis(tert-butoxycarbonyl)gemcitabine in 15 mL of dry THF was added 0.4 mL (2.5 mmol) of diisopropylethyl amine followed by 0.2 mL (2.5 mmol) of chloroacetyl chloride, at −8.0° C. with stirring under Ar. TLC after 0.5 hour (10% acetone in CHCl$_3$) indicated a complete reaction and at 40 min the reaction mixture was quenched with 20 drops of isopropyl alcohol and warmed to room temperature. THF was removed in vacuo and residue was taken up into 40 mL of CHCl$_3$ and washed with 10 mL of water, dried with sodium sulfate, and the solvent was removed in vacuo to give a foamy semi-solid.

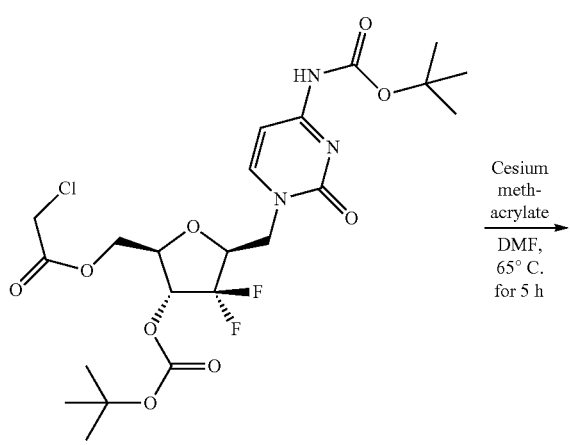

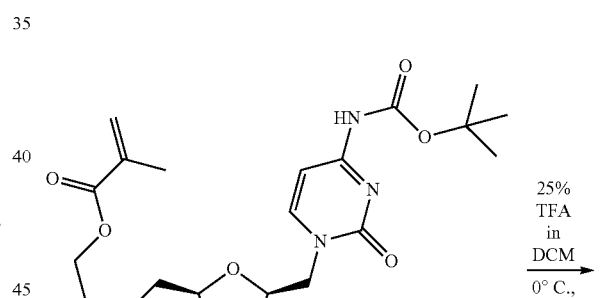

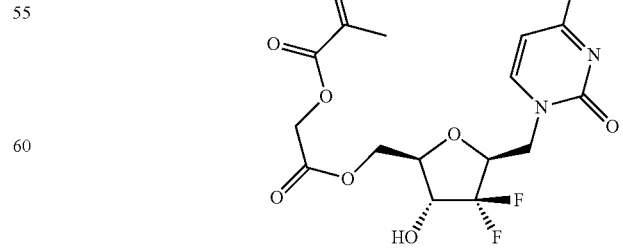

2''-methacryoyl-5-O-glycolyl-Gemcitabine: To 45 mg of methacryoyl-5'-O-glycolyl-4-N-3'-O-bis(tert-butoxycarbonyl)gemcitabine in 1.5 mL of dry methylene chloride was added 0.5 mL of trifluoroacetic acid dropwise at 0° C. with stirring under Ar. The reaction mixture was placed in a freezer overnight at −4° C. and in the morning the solvent was removed in vacuo. Then, repeated evaporations of 5 mL portions of methylene chloride were performed. After treating with several mL of triethyl amine and evaporating the excess, gradient silica gel chromatography with methylene chloride/acetone:9/1 to methylene chloride/acetone/ethanol: 5/4/1 gave 35 mg, NMR (acetone-d6/D$_2$O) consistent with proposed structure of 2″-methacryoyl-5′-O-glycolyl-gemcitabine.

Example 11

Preparation of a Polymerizable Pharmaceutical Agent

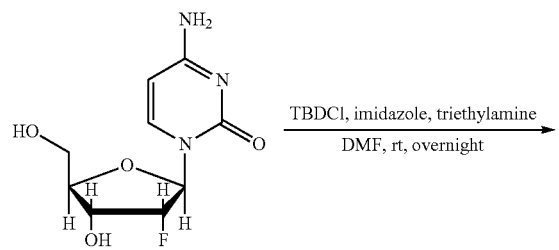

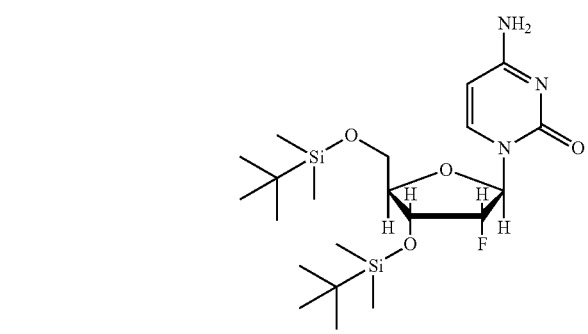

Preparation of 3′,5′-O-Bis-(tert-butyldimethylsilyl)-gemcitabine: To a stirring solution of gemcitabine hydrochloride (12 g, 40 mmol) in anhydrous dimethylformamide (240 mL) was added imidazole (8.17 g, 120 mmol) and tert-butyldimethylsilyl chloride (21.1 g, 140 mmol) sequentially. To the resulting solution was added trimethylamine (6.13 mL, 44 mmol) dropwise. The solution was stirred under room temperature for 15 hours. Then the reaction was filtered over a fritted glass funnel, and the filtrate was concentrated using a rotary evaporator. The residue was suspended in ethyl acetate (200 mL). The organic phase was washed with saturated sodium bicarbonate solution (200 mL×1) and then saturated sodium chloride solution (200 mL×1), before being dried over sodium sulfate. The solvent was removed using a rotary evaporator to afford the product as a yellow syrup (22.56 g).

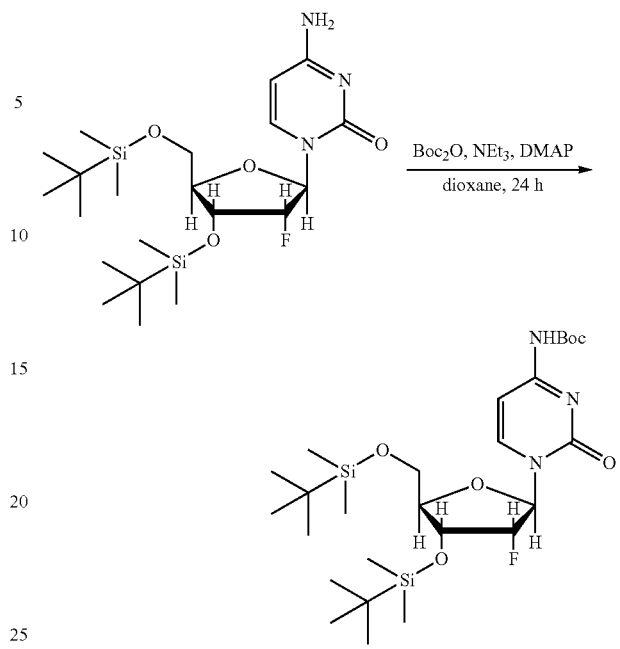

Preparation of 3′,5′-O-Bis-(tert-butyldimethylsilyl)-4-N-Boc-gemcitabine: To a solution of 3′,5′-O-bis-(tert-butyldimethylsilyl)-gemcitabine (3.04 g, 6.18 mmol) in dioxane (24 mL) was added 4-dimethylaminopyridine (105 mg, 0.86 mmol), triethylamine (5.2 mL, 37.1 mmol), and Di-tert-butyl dicarbonate (2.13 mL, 9.27 mmol). The reaction was stirred for 24 hours. Upon completion, it was poured over 60 mL ethyl acetate and washed with 75 mL saturated aqueous NaHCO$_3$ solution. The organic fraction was dried over Na$_2$SO$_4$. The crude product (3.87 g) was separated using flash chromatography to afford the product as a clear solid (1.67 g, 45.6%).

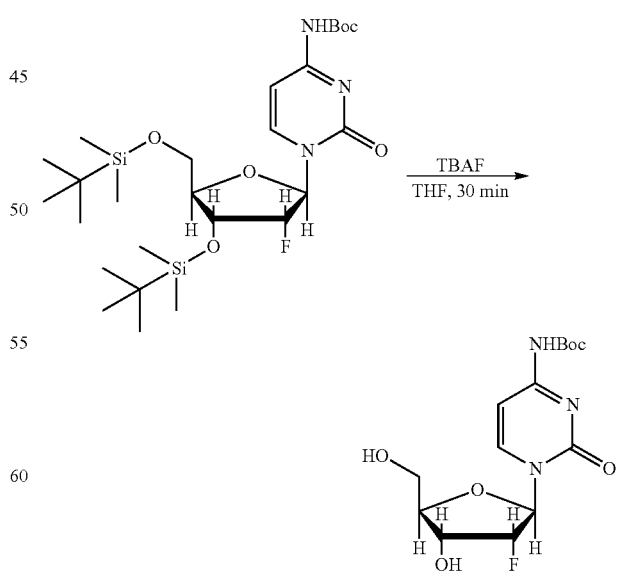

Preparation of the 4-N-Boc gemcitabine: To a stirring solution of 3′,5′-O-Bis-(tert-butyldimethylsilyl)-4-N-Bocgemcitabine (7.67 g) in THF (477 mL) was added tetrabutylammonium fluoride (1 M in THF, 28.6 mL). The reaction was stirred for 30 min. Upon completion, the solvent was removed on a rotary evaporator. The reaction was worked up according to a published procedure. The crude product was separated on column using a gradient of DCM and acetone to afford the product as clear crystals.

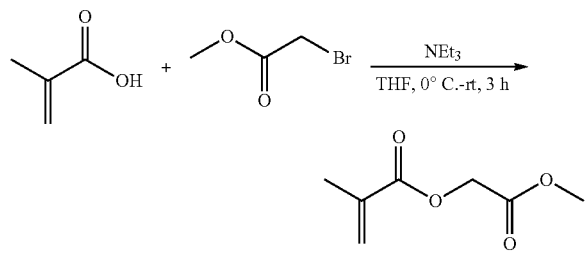

Preparation of carbomethoxymethyl methylacrylate: To a solution of 2-bromoacetic acid methyl ester (12.4 mL, 132.4 mmol) in THF (95 mL) at 0° C. was added methacrylic acid (9.3 mL, 110.4 mmol) and triethylamine (26.5 mL, 189.9 mmol). The reaction was then pulled out of the ice bath and stirred for 3 hours. Upon completion, a white precipitate was filtered off. The filtrate was kept and the solvent was removed on a rotary evaporator. The residue was resuspended in 100 mL H$_2$O, and the aqueous phase was extracted with ethyl acetate (100 mL×2). The combined organic fractions were washed with saturated sodium chloride solution (100 mL×1) and dried over Na$_2$SO$_4$. The solvent was removed on a rotary evaporator, and the residue was subjected to distillation to obtain the product as a clear liquid with a pleasant aroma (13.97 g, 87.8%).

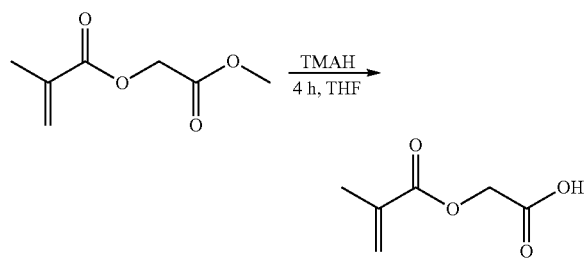

Preparation of carboxymethyl methacrylate: A solution of carbomethoxymethyl methylacrylate (10.85 g, 75.3 mmol) in THF (276.9 mL) and solution of tetramethylammonium hydroxide (2.38%, 276.9 mL) in H$_2$O (276.9 mL) were mixed and stirred for 3 hours. Then the solution was subjected to rotary evaporation to remove the THF. An aqueous solution of HCl (25%, 29 mL) was added to the aqueous phase to adjust the pH to approximately 3. The aqueous phase was extracted with ethyl acetate (200 mL×2). The ethyl acetate fraction was washed with H$_2$O (200 mL×1) and saturated NaCl solution (200 mL×1) successively. It was dried over Na$_2$SO$_4$ and the solvent was removed on a rotary evaporator. The crystals were washed with petroleum ether to afford the final product as clear crystals (9.89 g, 55.8%).

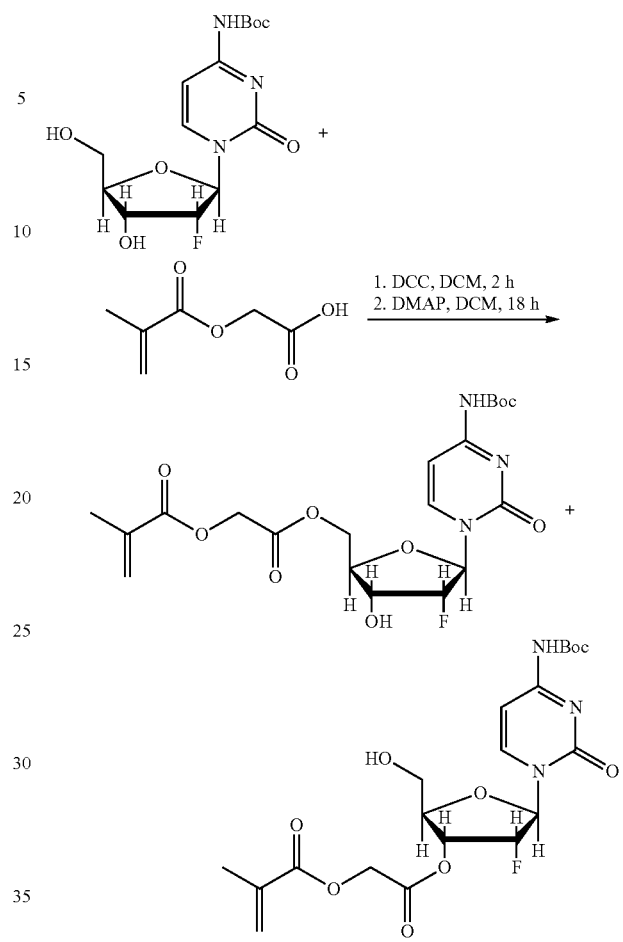

Preparation of 2″-methacryoyl-5′-O-glycolyl-4-N-Boc-Gemcitabine and 2″-methacryoyl-3′-O-glycolyl-4-N-Boc-Gemcitabine: To a solution of carboxymethyl methacrylate (0.25 g, 1.73 mmol) in DCM (10 mL) was added N,N′-dicyclohexylcarbodiimide (178.5 mg, 0.865 mmol). After 2 hours of stirring, a white precipitate was removed over a pad of celite. The filtrate was used directly for the next step. To a solution of 4-N-Boc gemcitabine (261.6 mg, 0.72 mmol) in DCM (10.6 mL) was added DMAP (8.8 mg, 0.072 mmol) and the filtrate. The reaction was stirred for 18 hours. Upon completion, it was washed with 5 mL saturated aqueous NaHCO$_3$ solution. The organic fraction was dried over Na$_2$SO$_4$ and the solvent was removed using a rotary evaporator. The crude product was separated using flash chromatography to obtain the final product as a mixture of the 3′- and 5′-isomers (87.6 mg, 24.8%).

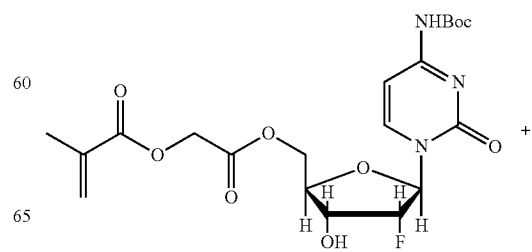

-continued

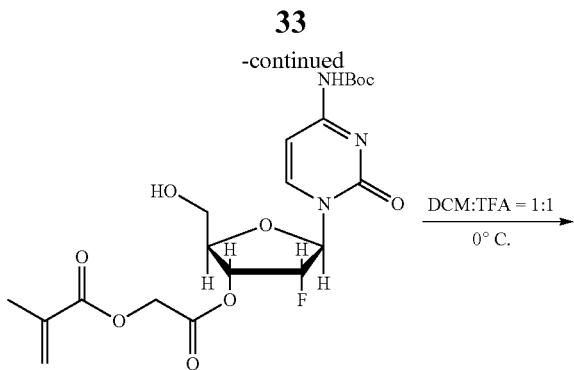

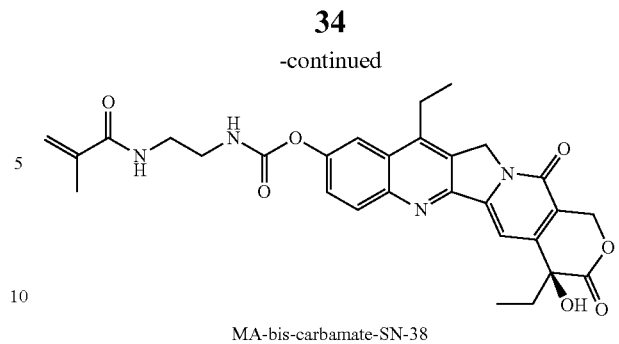

MA-bis-carbamate-SN-38

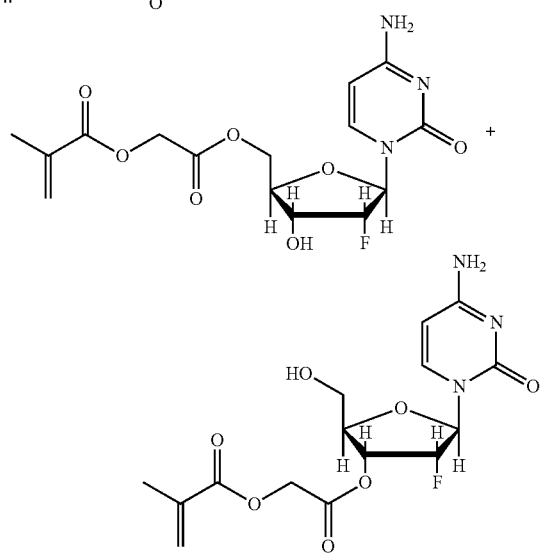

Preparation of 2"-methacryoyl-5'-O-glycolyl-Gemcitabine and 2"-methacryoyl-3'-O-glycolyl-Gemcitabine: To a solution of 2"-methacryoyl-5'-O-glycolyl-4-N-Boc-Gemcitabine (87 mg, 0.178 mmol) in DCM (0.89 mL) was added trifluoroacetic acid (0.89 mL) at 0° C. The solution was stirred for 3.5 hours. Upon completion, the solvent was removed using a rotary evaporator. The residue was resuspended in 5 mL ethyl acetate. The organic phase was washed successively with 5% NaHCO₃ solution (2.5 mL×2) and saturated NaCl solution (2.5 mL×1). The organic fraction was dried over Na₂SO₄ and the solvent was removed using a rotary evaporator. The crude product was separated using flash chromatography to afford the product as clear solids (32.9 mg, 47.5%).

Example 12

Preparation of a Polymerizable Active Pharmaceutical Agent

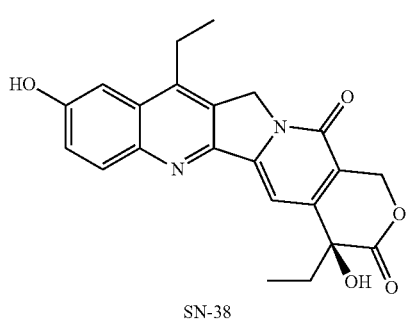

SN-38

To 3.9 g (10 mmol) of SN-38 in 500 mL dry THF, at 0° C. was added 1.74 mL (10 mmol) of diisopropylethylamine followed by 2.96 g (10 mmol) of triphosgene (Aldrich) in 100 mL of THF, drop wise over 0.5 hr. After 1 hour at 0° C., the reaction mixture was transferred to a rapidly stirred flask containing 1.8 g of N,N'-dimethylethylenediamine (50 mmol) in dry THF. After 1 hour at room temperature, the solvent was removed from the reaction mixture in vacuo followed by an evaporation of 100 mL of DMF in vacuo to remove excess amines. The residue was placed on the vacuum line overnight.

The next day, the residue from the vacuum line was dissolved into 500 mL of THF and 1.74 mL (10 mmol) of diisopropylethyl amine was added. After cooling the reaction mixture down to 0° C., 1.1 mL (1.15 mmol) of methacryloyl chloride was added in 100 mL of dry THF over 0.5 hour. After 1 hr of stirring at 0° C., the solvent was removed from the reaction mixture and the residue was flashed with 0-5% isopropyl alcohol in methylene chloride, to give the desired MA-bis-carbamate-SN-38 product.

Example 13

Preparation of a Polymerizable Active Pharmaceutical Agent

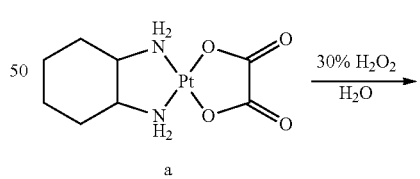

a

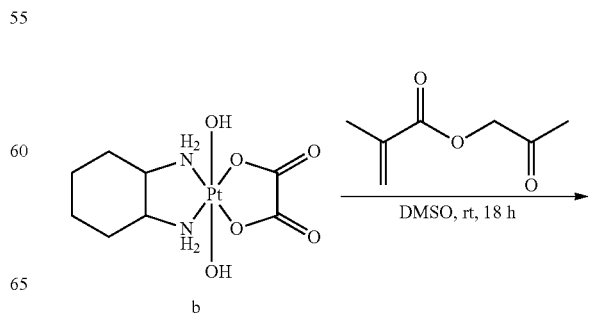

b

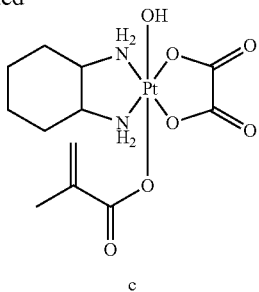

c

To a 50 mL water suspension of 2.5 g oxaliplatin a (6.30 mmol) being stirred for 10 minutes at 50° C., 125 mL of 30% H₂O (1.22 mol) was slowly added as stirring at 50° C. continued. After the reaction mixture became homogeneous, the reaction was continued for an additional hour. Charcoal was added to deactivate the residual H₂O and the mixture was stirred at room temperature overnight. Charcoal was removed by filtration and the water was removed under vacuum to obtain the dihydroxy oxaliplatin, b, which is a white solid. To a 100 mL anhydrous DMSO suspension of 800 mg dihydroxy oxaliplatin, b (1.856 mmol), 20 mL solution of 288 mg methacrylic anhydride (1.87 mmol) in anhydrous DMSO was added dropwise. The reaction mixture was stirred overnight at room temperature and became homogeneous. The DMSO was concentrated under vacuum at 55° C. till approximately 5 mL of solution was left. The product was precipitated by adding 200 mL of ether into the crude solution and stirring overnight. The solid was then collected via filtration and dried under vacuum for 8 hours. A total of 1.06 g of monohydroxy monomethacrylate oxaliplatin, c, was obtained with quantitative yield.

Example 14

Preparation of a Hydrogel Filament with Incorporated Active Agent

To prepare a hydrogel filament with an incorporated active agent, 0.71 g of the polymerizable active agent prepared in example 8, 0.3 g of the material described in Example 4, 0.2 g of TMP lac/gly, and 0.02 g of azobisisobutyronitrile were dissolved in 1.25 g of dimethylformamide. The solution was sparged with argon for 10 min before injection into 0.045 inch ID HYTREL® tubing using a 1 cc syringe. The tubes were heat sealed at both ends and placed in a 100° C. water bath for 1 hr, then overnight in an 80° C. oven to polymerize the solution.

The hydrogel was removed by swelling the tubing in chloroform allowing the filament to be peeled from the tube. The hydrogel was washed in isopropanol for 1 hr to remove any unreacted components, then vacuum dried for 72 hr at room temperature to remove any residual alcohol.

Example 15

Preparation of a Hydrogel Filament with Incorporated Active Agent

Samples of gemcitabine loaded filaments prepared as described in Example 1, Example 7, and Example 10 were placed in 5 mL of saline and incubated at 37° C. At various time points, the saline was sampled and exchanged with fresh saline. The amount of gemcitabine in the saline samples was determined by high performance liquid chromatography and illustrated in the Table below and in FIG. 1.

|  | mg gemcitabine eluted | | |
| --- | --- | --- | --- |
| Time | Example 1 | Example 7 | Example 10 |
| 1 hr | 4.03 | 5.07 | 0.05 |
| 2 hr | 0.26 | 1.54 | 0.01 |
| 5 hr | 0.05 | 0.41 | 0 |
| 20 hr | 0.02 | 0.02 | 0.01 |
| 24 hr | 0 | 0 | 0 |
| 72 hr | 0 | 0 | 0.08 |
| 7 d | 0 | 0 | 0.48 |
| 13 d | 0 | 0 | 1.06 |
| 15 d | 0 | 0 | 0.4 |
| 17 d | 0 | 0 | 0.36 |
| 21 d | 0 | 0 | 0.97 |
| 24 d | 0 | 0 | 0.31 |
| 28 d | 0 | 0 | 1.92 |
| 31 d | 0 | 0 | 0.72 |
| 36 d | 0 | 0 | 0.58 |
| 38 d | 0 | 0 | 0.14 |
| 46 d | 0 | 0 | 0.71 |

The results illustrate the potential difference between quick, short term release by entrapping or loading the drug into the filament and a slow long term release by incorporating the drug into the hydrogel filament.

The preceding disclosures are illustrative embodiments. It should be appreciated by those of skill in the art that the devices, techniques and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of forming a therapeutic polymer filament comprising:
   reacting a prepolymer solution including:
   at least one macromer selected from ethoxylated pentaerythritol, ethoxylated trimethylolpropane, or a combination thereof,
   at least one visualization agent, and
   a polymerizable pharmaceutical agent having a structure

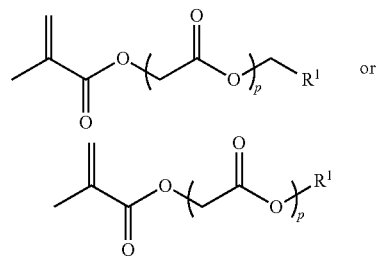

wherein $R^1$ is wherein each $R^2$ and $R^3$ can independently be H, $CH_3$, $C_2$-$C_6$ alkyl, $C_2$-$C_6$ substituted with a halogen or other $C_1$-$C_6$ alkyl, $NH_2$, $CO_2$, ON, $CF_3$, F, Cl, Br, I, $CCl_3$, OH, or $CH_2OH$;

n is 1, 2, 3, or 4;

m is 1, 2, 3, or 4;

$X^1$, $X^2$, $X^3$, and $X^4$ are each N or CH; and $X^5$ is O, $CH_2$, or NH; and p is 0, 1, 2, 3 or 4 thereby forming the therapeutic polymer filament wherein the polymerizable pharmaceutical agent is chemically bound to the therapeutic polymer filament.

2. The method of claim 1, further comprising adding at least one crosslinker to the prepolymer solution, wherein the at least one crosslinker includes an ester, a carbonate, a thioester, or a combination thereof.

3. The method of claim 1, further comprising adding at least one monomer to the prepolymer solution, wherein the at least one monomer is t-butyl acrylamide, 2-hydroxyethyl methacrylate, hydroxyl propyl acrylate, hydroxyl butylacrylate, or a combination thereof.

4. The method of claim 3, wherein the at least one monomer has a concentration of between about 5% and about 40% w/w of the prepolymer solution.

5. The method of claim 1, wherein the at least one macromer has a concentration of between about 15% and about 25% w/w of the prepolymer solution or has a molecular weight of between about 100 g/mole and about 5,000 g/mole.

6. The method of claim 1, wherein the at least one visualization agent is barium, bismuth, tantalum, platinum, gold, iodine-containing molecules, barium sulfate, or a combination thereof.

7. The method of claim 1, wherein the at least one visualization agent is an iodine-containing molecule.

8. A method of forming a therapeutic polymer filament comprising:
reacting a prepolymer solution including:
at least one macromer selected from poly(ethylene glycol), poly(propylene glycol), poly(tetramethylene oxide), ethoxylated pentaerythritol, ethoxylated trimethylolpropane, poly(vinyl alcohol), or a combination thereof, and
a polymerizable pharmaceutical agent having a structure

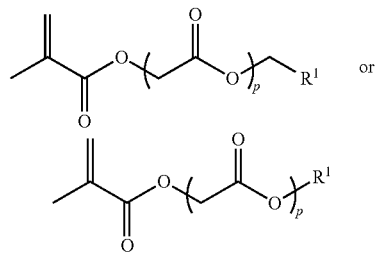

wherein $R^1$ is

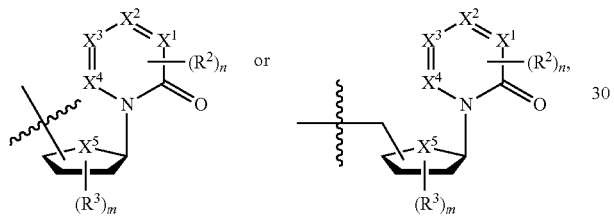

wherein each $R^2$ and $R^3$ can independently be H, $CH_3$, $C_2$-$C_6$ alkyl, $C_2$-$C_6$ substituted with a halogen or other $C_1$-$C_6$ alkyl, $NH_2$; $CO_2$, ON, $CF_3$, F, Cl; Br, I, $CCl_3$, OH, or $CH_2OH$;
n is 1, 2, 3, or 4;
m is 1, 2, 3, or 4;
$X^1$, $X^2$, $X^3$, and $X^4$ are each N or CH; and
$X^5$ is O, $CH_2$, or NH; and
p is 0, 1, 2, 3 or 4
thereby forming the therapeutic polymer filament wherein the polymerizable pharmaceutical agent is chemically bound to the therapeutic polymer filament.

9. The method of claim 8, further comprising adding at least one monomer to the prepolymer solution, wherein the at least one monomer is t-butyl acrylamide, 2-hydroxyethyl methacrylate, hydroxyl propyl acrylate, hydroxyl butylacrylate, or a combination thereof.

10. The method of claim 9, wherein the at least one monomer has a concentration of between about 5% and about 40% w/w of the prepolymer solution.

11. The method of claim 8, wherein the at least one macromer has a concentration of between about 15% and about 25% w/w of the prepolymer solution or has a molecular weight of between about 100 g/mole and about 5,000 g/mole.

12. The method of claim 8, further comprising at least one visualization agent in the prepolymer solution.

13. The method of claim 12, wherein the at least one visualization agent is barium, bismuth, tantalum, platinum, gold, iodine-containing molecules, barium sulfate, or a combination thereof.

14. The method of claim 12, wherein the at least one visualization agent is an iodine-containing molecule.

15. The method of claim 8, further comprising at least one crosslinker, wherein the at least one crosslinker includes an ester, a carbonate, a thioester, or a combination thereof.

16. A method of forming a therapeutic polymer filament comprising:
reacting a prepolymer solution including:
at least one macromer selected from polyethylene glycol), poly(propylene glycol), poly(tetramethylene oxide), ethoxylated pentaerythritol, ethoxylated trimethylolpropane, poly(vinyl alcohol), or a combination thereof, and
a polymerizable pharmaceutical agent having a structure

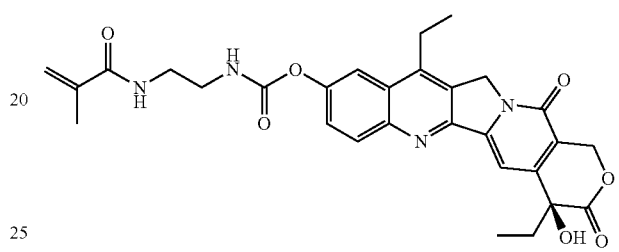

or

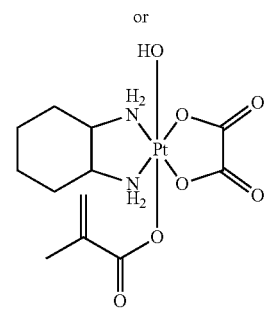

thereby forming the therapeutic polymer filament wherein the polymerizable pharmaceutical agent is chemically bound to the therapeutic polymer filament.

17. The method of claim 16, further comprising adding at least one monomer to the prepolymer solution, wherein the at least one monomer is t-butyl acrylamide, 2-hydroxyethyl methacrylate, hydroxyl propyl acrylate, hydroxyl butylacrylate, or a combination thereof.

18. The method of claim 17, wherein the at least one monomer has a concentration of between about 5% and about 40% w/w of the prepolymer solution.

19. The method of claim 16, wherein the at least one macromer has a concentration of between about 15% and about 25% w/w of the prepolymer solution or has a molecular weight of between about 100 g/mole and about 5,000 g/mole.

20. The method of claim 16, further comprising at least one visualization agent in the prepolymer solution.

21. The method of claim 20, wherein the at least one visualization agent is barium, bismuth, tantalum, platinum, gold, iodine-containing molecules, barium sulfate, or a combination thereof.

22. The method of claim 20, wherein the at least one visualization agent is an iodine-containing molecule.

23. The method of claim 16, further comprising at least one crosslinker, wherein the at least one crosslinker includes an ester, a carbonate, a thioester, or a combination thereof.

* * * * *